US009309247B2

(12) United States Patent
Lee et al.

(10) Patent No.: US 9,309,247 B2
(45) Date of Patent: Apr. 12, 2016

(54) 2-SUBSTITUTED IMIDAZO[4,5-D]PHENANTHROLINE DERIVATIVES AND THEIR USE IN THE TREATMENT OF CANCER

(71) Applicant: Aptose Biosciences Inc., Toronto (CA)

(72) Inventors: Yoon Lee, Mississauga (CA); Howard Cukier, Stoney Creek (CA); Venkata Nedunuri, Mississauga (CA); Robert Peralta, Mississauga (CA); Mario Huesca, Toronto (CA); Aiping H. Young, Toronto (CA)

(73) Assignee: LORUS THERAPEUTICS INC. (CA)

( * ) Notice: Subject to any disclaimer, the term of this patent is extended or adjusted under 35 U.S.C. 154(b) by 0 days.

(21) Appl. No.: 14/777,198

(22) PCT Filed: Mar. 20, 2014

(86) PCT No.: PCT/US2014/031349
§ 371 (c)(1),
(2) Date: Sep. 15, 2015

(87) PCT Pub. No.: WO2014/153464
PCT Pub. Date: Sep. 25, 2014

(65) Prior Publication Data
US 2016/0031883 A1 Feb. 4, 2016

Related U.S. Application Data

(60) Provisional application No. 61/803,627, filed on Mar. 20, 2013.

(51) Int. Cl.
*A61K 31/4745* (2006.01)
*C07D 471/12* (2006.01)
*C07D 471/14* (2006.01)

(52) U.S. Cl.
CPC .................................. *C07D 471/14* (2013.01)

(58) Field of Classification Search
USPC ........................................... 514/287; 546/64
See application file for complete search history.

(56) References Cited

U.S. PATENT DOCUMENTS

| | | |
|---|---|---|
| 3,279,918 A | 10/1966 | Cassiers et al. |
| 3,297,710 A | 1/1967 | Silversmith |
| 3,714,181 A | 1/1973 | Lantos |
| 4,089,747 A | 5/1978 | Bruschi |
| 4,423,046 A | 12/1983 | Carlson |
| 4,466,976 A | 8/1984 | Klose et al. |
| 4,585,771 A | 4/1986 | Klose et al. |
| 4,705,855 A | 11/1987 | Desideri et al. |
| 4,721,670 A | 1/1988 | Osada et al. |
| 4,758,421 A | 7/1988 | Chang et al. |
| 4,902,705 A | 2/1990 | Hiota et al. |
| 4,970,226 A | 11/1990 | Sun et al. |
| 5,011,472 A | 4/1991 | Aebischer |
| 5,023,252 A | 6/1991 | Hseih |
| 5,024,935 A | 6/1991 | McClune et al. |
| 5,047,318 A | 9/1991 | Snyder et al. |
| 5,161,389 A | 11/1992 | Rockenfeller et al. |
| 5,328,671 A | 7/1994 | Rockenfeller et al. |
| 5,441,716 A | 8/1995 | Rockenfeller et al. |
| 5,496,702 A | 3/1996 | Bishop et al. |
| 5,501,959 A | 3/1996 | Lancaster et al. |
| 5,514,550 A | 5/1996 | Findlay et al. |
| 5,656,644 A | 8/1997 | Adams et al. |
| 5,686,455 A | 11/1997 | Adams et al. |
| 5,693,589 A | 12/1997 | Goswami et al. |
| 5,700,826 A | 12/1997 | Mjalli et al. |
| 5,753,687 A | 5/1998 | Mjalli et al. |
| 5,809,775 A | 9/1998 | Tarabulski et al. |
| 5,916,891 A | 6/1999 | Adams et al. |
| 5,945,418 A | 8/1999 | Bemis et al. |
| 6,060,216 A | 5/2000 | Ichikawa et al. |
| 6,117,609 A | 9/2000 | Maeda |
| 6,194,441 B1 | 2/2001 | Roberts et al. |
| 6,266,955 B1 | 7/2001 | Liang et al. |
| 6,268,370 B1 | 7/2001 | Adams et al. |
| 6,288,212 B1 | 9/2001 | Hancock |
| 6,521,655 B1 | 2/2003 | Beers et al. |
| 6,589,966 B1 | 7/2003 | Torti et al. |
| 6,852,727 B2 | 2/2005 | Goulet et al. |
| 7,115,645 B2 | 10/2006 | Halfbrodt et al. |
| 7,291,404 B2 | 11/2007 | Aziz et al. |
| 7,718,685 B2 | 5/2010 | Shin et al. |
| 7,884,120 B2 | 2/2011 | Al-Qawasmeh |
| 7,888,118 B2 | 2/2011 | Shin et al. |

(Continued)

FOREIGN PATENT DOCUMENTS

| | | |
|---|---|---|
| CA | 2351694 | 7/1993 |
| CN | 1289774 | 4/2001 |

(Continued)

OTHER PUBLICATIONS

Decision to Grant Chinese Patent Application 201010168726.8, dated Nov. 6, 2013.
Decision to Grant European for Patent Application No. EP03787546, dated May 22, 2014.
Gao, D., et al., "Synthesis and electroluminescence properties of an organic europimn complex," Journal of Alloys and Compounds, 358(1-2): 188-192, 2003.
Xiong, Ya, et al., "Interaction of polypyridyl mthenium(II) complexes containing non-planar ligands with DNA," J. Chem. Soc, 1:19-24, 1999.
Xu, et al., Synthesis and spectroscopic RNA binding studies of [Ru(phen)2MIIPIP]<2+>, Inorganic Chemistry Communications, Amsterdam, 6(6):766-768, 2003.
Goto et al., Improved efficacy with nonsimultaneous administration of netilmicin and minocycline against methicillin-resistant *Staphylococcus aureus* in in vitro and in vivo models; International Journal of Antimicrobial Agents; 1999; 11 :39-46; International Society of Chemotherapy; Elsevier Science B,V.; United Kingdom.
Horig et al. Journal of Translational Medicine 2004, 2(44).

(Continued)

*Primary Examiner* — Charanjit Aulakh
(74) *Attorney, Agent, or Firm* — Cooley LLP

(57) ABSTRACT

The present invention provides 2-substituted imidazo[4,5-d] phenanthroline compounds, which are capable of inhibiting proliferation of one or more renal cancer cells, pancreatic cancer cells, prostate cancer cells, colon cancer cells, leukemia cells, brain cancer/tumor cells or non-small cell lung cancer cells.

27 Claims, 4 Drawing Sheets

(56) References Cited

U.S. PATENT DOCUMENTS

| | | | |
|---|---|---|---|
| 7,989,089 | B2 | 8/2011 | Wang et al. |
| 8,148,392 | B2 | 4/2012 | Huesca et al. |
| 8,357,678 | B2 * | 1/2013 | Mei .................... C07F 15/0053 514/185 |
| 8,394,815 | B2 | 3/2013 | Al-Qawasmeh |
| 2002/0006948 | A1 | 1/2002 | Halfbrodt et al. |
| 2002/0119955 | A1 | 8/2002 | Doyle et al. |
| 2004/0127527 | A1 | 7/2004 | Hongu et al. |
| 2004/0176601 | A1 | 9/2004 | Goulet et al. |
| 2004/0265628 | A1 | 12/2004 | Wang et al. |
| 2005/0282285 | A1 | 12/2005 | Radhamohan et al. |
| 2007/0105929 | A1 | 5/2007 | Al-Qawasmeh |
| 2007/0123553 | A1 | 5/2007 | Huesca et al. |
| 2011/0152337 | A1 | 6/2011 | Al-Qawasmeh |
| 2013/0177632 | A1 | 7/2013 | Al-Qawasmeh |

FOREIGN PATENT DOCUMENTS

| | | |
|---|---|---|
| CN | 1289775 | 4/2001 |
| DE | 3141063 | 4/1983 |
| DE | 3422175 | 12/1985 |
| DE | 10323591 | 12/2004 |
| EP | 0077024 A2 | 4/1983 |
| EP | 0165 588 | 12/1985 |
| EP | 0165588 | 12/1985 |
| EP | 0812 829 | 12/1997 |
| EP | 0812829 | 12/1997 |
| EP | 1428831 | 6/2004 |
| JP | 58-109474 A | 6/1983 |
| JP | 02-258017 | 10/1990 |
| JP | 11-199582 A | 7/1999 |
| JP | 2000-273088 | 10/2000 |
| JP | 2001-506997 A | 5/2001 |
| JP | 2002-275458 | 9/2002 |
| JP | 2002-364578 | 12/2002 |
| JP | 2004-528206 | 9/2004 |
| JP | 2004-530731 | 10/2004 |
| JP | 2006-503817 | 2/2006 |
| WO | WO 93/14081 | 7/1993 |
| WO | WO 94/11685 | 5/1994 |
| WO | WO 95/03297 | 2/1995 |
| WO | WO 96/18626 | 6/1996 |
| WO | WO 9736587 | 3/1997 |
| WO | WO 97/36587 | 10/1997 |
| WO | WO 98/14081 | 4/1998 |
| WO | WO 98 27065 A | 6/1998 |
| WO | WO 98/27108 | 6/1998 |
| WO | WO 99/01128 | 1/1999 |
| WO | WO 99/01205 | 1/1999 |
| WO | WO 9902155 | 1/1999 |
| WO | WO 9907701 | 2/1999 |
| WO | WO 00/33836 | 6/2000 |
| WO | WO 0059541 | 10/2000 |
| WO | WO 00/68206 A1 | 11/2000 |
| WO | WO 00/68266 | 11/2000 |
| WO | WO 0078761 A1 | 12/2000 |
| WO | WO 0126467 | 4/2001 |
| WO | WO 0224680 | 3/2002 |
| WO | WO 0246168 A1 | 6/2002 |
| WO | WO 02/072576 | 9/2002 |
| WO | WO 02072086 | 9/2002 |
| WO | WO 03004023 A | 1/2003 |
| WO | WO 03032984 | 4/2003 |
| WO | WO 03/066579 | 8/2003 |
| WO | WO 03087026 | 10/2003 |
| WO | WO 2004005264 | 1/2004 |
| WO | WO 2004/016086 A2 | 2/2004 |
| WO | WO 2004/042207 | 5/2004 |
| WO | WO 2005/047266 A1 | 5/2005 |
| WO | WO 2006/012903 | 2/2006 |
| WO | WO 2006/081824 | 8/2006 |
| WO | WO 2006/126177 A2 | 11/2006 |
| WO | WO 2007/000170 | 1/2007 |

OTHER PUBLICATIONS

CAS Registry No. 330449-52-0, entered in CAS Registry on Apr. 6, 2001.

Registry No. 416872-13-4, entered into Registry file in SIN on May 16, 2002.

Requirement for Restriction/Election in U.S. Appl. No. 10/525,690 dated Jul. 20, 2009.

Harnish R. Michie; The value of animal models in the development of new drugs for the treatJnent of the sepsis syndrome; Journal for Antimicrobial Chemotherapy; 1998; 41: 47-49; British Society for Antimicrobial Chemotherapy; Birmingham, UK.

Steve Sternberg; The Emerging Fungal Threat; Science; 1994; 266: 1632-1634; American Association for the Advancement of Science; Washington, DC, USA.

Thaler et al.; Evaluation ofSingle-Drug and Combination Antifungal Therapy in an Experimental Model of Candidiasis in Rabbits with Prolonged Netropenia; The Journal of Infectious Diseases; 1988; 158: 80-88; University of Chicago Press; Chicago, IL, USA.

Totsuka et al.; Combined effects of vancomycin and Imipenem against methicillin-resistant *Staphylococcus aureus* (MRSA) in vitro and in vivo; Journal of Antimicrobial Chemotherapy; 1999; 44: 455-460; The British Society for Antimicrobial Chemotherapy; Birmingham, UK.

Walsh et al; Effects of Preventive, Early, and Late Antifungal Chemotherapy with Fluconazole in Different Granulocytopenic Models ofExperimental Disseminated Candidiasis; The Journal ofInfectious Diseases; 1990; 161:7 55-7 60; University of Chicago Press; Chicago, IL, USA.

Isikdag et al.; QSAR of Inhibitory Activities by 2,4,5-Trisubstituted Imidazole Derivatives on Tubifex Worms; Acta Pharmaceutica Turcica; 1995; 37(1): 19-24.

Arroyo et al.; Therapy of Murine Aspergillosis with Amphotericin B in Combination with Rifampin or 5-Fluorocystosine; Antimicrobial Agents and Chemotherapy; 1977; pp. 21-25; American Society for Microbioloty; Washington, DC, USA.

Xiu R. Bu et al.; A Novel Approach to Synthesis of Tricyanovinylthiophene for heterocyclic Imidazole Nonlinear Optical Chromophores; Tetrahedron Letters; 1996; 37: 7331-7334; Elsevier Science Ltd.; London, UK.

Diekema et al; Survey ofInfections due to *Staphylococcus* Species: Frequency ofOccurence and Antimicrobial Susceptibility of Isolates Collected in the United States, Canada, Latin America, Europe, and the Western Pacific Region for the SENTRY Antimicrobial Surveillance Program, 1997-1999; Clinical Infectious Diseases; 2001; 32: S114-132; University of Chicago Press; Chicago, IL, USA.

Hoban et al.; Worldwide Prevalence of Antimicrobial Resistance in *Streptococcus pneumoniae*, HKaemophilus influenzae, and Moraxella catarrhalis in the SENTRY Antimicrobial Surveillance Program, 1997-1999; Clinical Infectious Diseases; 2001: 32:S81-93; Infec-tious Disease Society of America; The University of Chicago Press; Chicago, IL, USA.

Huesca etal; Adhesion and Virulence Properties of Epidemic Canadian Methicillin-Resistant *Staphylococcus au reus* Strain 1: Identification of Novel Adhesion Functions Associated with Plasmin-Sensitive Surface Protein; The Journal of Infectious Disease; 2002; Infectious Diseases Society of America; The University of Chicago, IL, USA.

Iwahi et al.; Virulence of *Escherichia coli* in Ascending Urinary-Tract Infection in Mice; Journal of Medical Microbiology; 1982; 15:303-316; The Society for General Microbiology; High Wire Press.

Database WPI; Section Ch. Week 199940, Derwent Publications Ltd., London, GB, AN 1999-474062 (XP002268773) & JP 11199582 (english abstract) A (Sagami Chern Res Cent), Jul. 27, 1999.

Klose et al.; The Suckling Mouse Model of Cholera; Trends in Microbiology; 2000; 8:189-91; Elsevier Science Ltd.

Schafer et al., Drug Discovery Today, 2008, 13 (21/22), 913-916.

Downey et al., "Degradation of DNA by 1,-10-phenanthroline," Biochem Biophys Res Commun, 1980, 93(1):264-70.

(56) References Cited

OTHER PUBLICATIONS

C.G. Wermuth, Hiroshi Nagase (translation supervisor), Saishin Spyaku Kagaku, Jo kan, Technomics Corporation, Jan. 1998. p. 243-248 (Japanese Version)—(Corresponding to C. G. Wermuth, The Practice of Medicinal Chemistry, Molecular Variations Based on Isosteric Replacements, 1996, 203-237, Academic Press (English version).

Ekwall, Bjorn; Screening of Toxic Compounds in Mammalian Cell Cultures; Annals New York Academy of D Sciences; 1983; 407: 64-77; Blackwell Publishing.

Isikdag et al., "Synthesis and analgesic activities of 2-substitutes-1H-phenantro [9,10-d]imidazoles," Boll. Chim. Farmaceutico, vol. 138 (1999) pp. 453-456.

Kimura et al., "Preparation of 4-(4.5-diphenyl-JH-imidazol-2-yl)benzaldehyde and its Practical Synthetic Use in the Synthesis of Unsymmetrically Substituted Imidazoles", Department of Chemistry, Okayama University, Okayama Japan, ITE Letters on Batteries, New Technologies & Medicine, 2002, 3(1), pp. 30-34.

LoGrasso et al., "Kinetic mechanism fro p38 MAP kinase," Biochem-isuy, 1997, 36:10422-10427.

Moylan et al., "Synthesis and Nonlinear Optical Properties of Donor-Acceptor Substituted TriarylAzole Derivatives", Almaden Res. Cent. IBM, San Jose, CA, USA, ChemistryofMaterials, 1993, 5(10): 1499-1508.

Pechkin, A.A. el, al., Synthesis and Properties of 2-(2-Furyl)-and 2-(2-Thienyl)-1-methylphenanthro[9, 1 0-d]imidazoles, Russian Journal of Organic Chemistry (Translation ofZhumal Organicheskoi Khimii), 2002, 38(5):726-730.

Registry No. 309285-51-6, entered into Registry file in SIN on Dec. 18, 2000.

CAS Registry No. 309285-51-6, entered in CAS Registry on Dec. 18, 2000.

Registry No. 332148-67-1, entered into Registry file in SIN on Apr. 24, 2001.

CAS Registry No. 332148-67-1, entered into CAS Registry on Apr. 24, 2001.

Registry No. 404904-57-0, entered into Registry file in SIN on Apr. 10, 2002.

CAS Registry No. 404904-57-0, entered in CAS Registry on Apr. 10, 2002.

Sarshar et al. "2,4,5-trisubstituted imidazoles: Novel nontoxic modulators of P-glycoprotein mediated multidmg resistance Part 1," Bioorg. Med. Chem. Lett., 2000, 10:2599-2601.

Simor et al.; 1999 Canada Communicable Disease Report, 25: 105-108.

Tanaseichuk et al.; Uch. Zap., Mord. Univ. (1971 ), No. 81, 95-7 (From: Ref. Zh., Khim, 1972, Abstr. No. 12zh318 D (English abstract).

Xu et al., "Effects of the ancillary ligands of polypyridyl mthenium (ii) complex(es) on the DNA-binding behaviors," New J. Chern., 2003, 27:1255-1263.

Zhang et al.; 2,4,5-TrisumstitutedImidazoles: Novel Nontoxic Modu-lators of P-glycoprotein Mediated Multidmg Resista11ce, Part 2; Bioorga11ic & Medicinal Chemistry Letters; 2000; 1 0: 2603-2605; Elsevier Science Ltd; Philadelphia, PA USA.

Lantos, "Reaction of Phenanthrenequinone with Ammonitun Acetate," J. Org. Chem., 40(11)1641-1642 (1975).

Pan et al., "DNA-binding proteins as site-specific nucleases," Mol Microbial, 1994, 12(3):335-42.

Sigman et al., "Oxygen-dependent cleavage of DNA by the 1,10-phenanthroline cuprous complex," J Bioi Chern, 1979, 254(24): 12269-72.

Springman et al., "Zinc content and function in human fibroblast collegenase," Biochemistry, 1995, 34(48): 15713-20.

McLay etal; The Discovery of RPR 200765A, a p38 MAP Kinase Inhibitor Displaying a Good Oral Anti-Arthritic Efficacy; Bioorganic & Medicinal Chemistry; 2001; 9: 537-554; Elsevier Science Ltd; Amsterdam, The Netherlands.

Nippon Kagaku Zasshi 1971, 92, 365-370.

Lock et al., Molecular mechanisms of growth inhibition induced by novel aryl-imidazole compotmds in human cancer cells Presented at IBC's 91h Annual World Congress Dmg Discovery Technology Meet-ing (Boston Aug. 8-13, 2004) Abstract.

Press Release Lorus Therapeutics Inc., "Lorus Announces Discovery of Novel Low Molecular Weight Compounds with Anticancer and Antibacterial Activity," May 12, 2004.

Press Release Loms Therapeutics Inc. "Lorus Therapeutics Inc to Present Results of Novel Anticancer Small Molecule Studies," Aug. 9, 2004.

Abdel-Meguid et al., "An orally bioavailable HIV-1 protease inhibitor containing an imidazole-derived peptide bond replacement: Crystallographic and pha.nnacokinetic analysis," Chemistry, 1994, 33:11671-11677.

Armesto et al., "A new site selective synthesis of benzoin esters, synthesis of sylrunetrically and unsymmetrically substituted benzils," Synthesis, 1988, 799-801.

Botana et al.,"p-(JH-Phenanthro[9,10-d]imidazol-2-yl)-Substituted Calix[4]arene, a Deep Cavity for Guest Inclusion", Departmento de Quimica Organica, Universidad Autonoma de Madrid, Spain, Organic LetTers, 2004, 6(7):1091-1094.

Chao et al., Palladium catalyst in DMSO for the oxidation of tolans to benzils, Polyhedron, 2000, 1975-1983.

Chi et al., "Palladium catalyst in DMSO for the oxidation oftolans to benzils," Synth. Comm., 1994, 24(15), 2119-2122.

Cuenda, et al., "Activation of stress-activated protein kinase-3 (SAPK3) by cytokines and cellular stresses is mediated via SAPKK3 (MKK6); comparison of the specificities of SAPK3 and SAPK2 (RK/p38),"EMBO J., 1997, 16:295-305.

Cuenda, et al., "SB 203580 is a specific inhibitor of a MAP kinase homologue which is stimulated by cellular stresses and interleukin-1," Febs Lett, 1995, 364:229-33.

Demirayak et al., "Synthesis of Certain Derivatives of Ethyl a-[ (phenanthro [9, 1 0-d]imidazol-2-yl)phenoxy ]alkanoate", Acta Pharmaceutica Tt~rcica, 1989, 31(1):19-25.

Fischer et al., "Dissociation constants of the conjugate acids of substituted benzyl phenyl ketones and of alkyl-substituted benzophenomes," J. Am. Chem. Soc. 1961, 83:4208-4210.

Gales et al., "Characterization of Pseudomonas aeruginosa isolates: Occurense rates, antimicrobial susceptibility patterns, and molecular typing in the global SENTRY antimicrobial surveillance program, 1997-1999," Clin. Infect. Dis., 2001, 32:S146-155.

Guijarro et al., "The reaction of active zinc with organic bromides," J. Am. Chem. Soc., 1999, 121:4155-4157.

Heerding et al., "1,4-disubstituted imidazoles are potential antibacterial agents functioning as inhibitors of enoyl acyl carrier protein reductase (Fabl)," Bioorg. Med. Chern. Lett., 2001, 11:2061-2065.

Krieg et al., Synthesis and Semiconductor Properties of Aryl-substituted Imidazoles, Naturforsch. 1967, 22b: 132-141 (English translation).

Office Action Final Rejection for U.S. Appl. No. 10/525,590, mailed Jun. 4, 2010.

Registry No. 330449-64-4, entered into Registry file in STN on Apr. 6, 2001.

Low et al., Clinical Prevalence, Antimicrobial Susceptibility, and Geographic Resistance Patterns of Enerococci: Results from the SENTRY Antimicrobial Surveillance Program, 1997-1999; Clinical Infectious Diseases; 2001; 32: S133-145; University of Chicago Press; Chicago, IL, USA.

Michael A. Pfaller, MD and Wen Liang Yu, MD; Antifungal Susceptibility Testing: Infectious Disease Clinics of North America; 2001; 15: 1227-145; Elsevier; Philadelphia, PA, USA.

Pfaller et al., Antifungal Susceptibility Testing: Technical Advances and Potential Clinical Applications; Clinical Infectious Diseases; 1997; 24: 776-84; University of Chicago Press.

Shibata et al., Therapeutic efficacy of J-111, 225, a move! trans-3, 5-disubstituted pyrrolidinylthio-1 methylcarbapenem, against experimental murine systemic infections; Journal of Antimicrobial Chemotherapy; 2000; 45: 379-82; British Society of Antimicrobial Chemotherapy; Birmingham, UK.

(56) References Cited

OTHER PUBLICATIONS

Yanke et al.; A CD-1 mouse model of infection with *Staphylococcus aureus*: Influence of gender on infection with MRSA and MSSA isolates; Canada Journal of Microbiology; 2000; 46: 920-926; NrC Research Press website.
Ghannoum et al.; Susceptibility Testing of Fungi: Current Status of Correlation of in Vitro Data with Clinical Outcome; Journal of Clinical Microbiology; 1996; 34: 489-495; American Society for Microbiology; Washington, DC, USA.
Lechner et al.; Differential Production ofTNK by Kupffer cells after phagocytosis of *E. coli* and *C. albicans*; American Journal of Physiology; 1994; 10:1-8; American Physiological Society.
Office Action for U.S. Appl. No. 12/976,122, mailed Jun. 1, 2012.
Office Action for U.S. Appl. No. 12/976,122, mailed Jul. 18, 2012.
Office Action for U.S. Appl. No. 12/976,122, mailed Feb. 13, 2012.
Office Action for U.S. Appl. No. 12/976,122, mailed Sep. 14, 2011.
Office Action for U.S. Appl. No. 13/778,458, mailed Jul. 19, 2013.
Chaston, T.B. et al., Clin. Cancer Res., vol. 9(1) (2003) pp. 402-414.
Dang. D.T. et al., FEBS Lett., vol. 476 (2000) pp. 203-207.
Ghaleb, A.M. et al., Cell Res., vol. 15(2) (2001)pp. 92-96.
Kaczynski, J et al., Genome Bioi., vol. 4(2) (2003) p. 206.1-206.8.
Kindermann, B.F. et al., Biochem. Cell Biol., vol. 83(2) (2005) pp. 221-229.
Kindennann, B.F. et al., J. Nut., vol. 134(1) (2004) pp. 57-62.
Narla, G. et al., Science, vol. 294 (2001) pp. 2563-2566.
Ohnishi, S. et al., Biochem. Biophys. Res. Commun., vol. 308(2) (2003) pp. 251-256.
Pandya, A.Y. et al. Clin. Cancer Res., vol. 10(8) (2004) pp. 2709-2719.
Richardson, D.R. Crit. Rev. Oncol. Hematol., vol. 42(3) (2002) p. 267-281.
Shulman, A. et al., Chern. Biol. Interact, vol. 16(1) (1977) pp. 89-99.
Subramaniam, M. et al., J. Cell Biochem., vol. 68 (1998)pp. 226-236.
Wang, N. et al., Down-regulation of gut-enriched Krüppel-like factor expression in esophageal cancer, World J. Gastroenterol., vol. 8(6) (2002) 966-970.
Wei, D. et al., Cancer Res, vol. 65(7) (2005) pp. 2746-2754.
Yasunaga, J. et al., Cancer Res., vol. 64(17) (2004) pp. 6002-6009.
Zhao, R. et al., Role of zinc and iron chelation in apoptosis mediated by tachpyridine, an anti-cancer iron chelator, Biochem. Pharmacol., vol. 67(9) (2004) pp. 1677-1688.
Adams, J.L et al., "Phyriidinylimidazole Inhibitors of p38: cyclic N -1 Imidazole Substituents Enhance p38 Kinase Inhibition and Oral Activity," Bioorg. Med. Chern. Lett, vol. 11 (2001) pp. 2867-2870.
Lee et al., "A protein kinase involved in the regulation of infiarmnatmy cytokine biosynthesis," Nature, vol. 327 (Dec. 1994) pp. 739-746.
Lewis, J.R., "Muscarine, imidazole, oxazole, thiazole and peptide alkaloids, and other miscellaneous alkaloids," Nat. Prod. Rep., vol. 15 (1998) pp. 417-437.
Lewis, J.R., "Muscarine, imidazole, osazole, thiazole and peptide alkaloids, and other miscellaneous alkaloids," Nat. Prod. Rep., vol. 15 (1998) pp. 371-395.
Lewis, J.R., "Miscellaneous alkaloids: Amaryllidaceae, Sceletium, muscaTine, imidazole, oxazole, peptide and other miscellaneous alkaloids," Nat. Prod. Rep, vol. 16 (1999) pp. 389-418.
Office Action dated Jul. 20, 2009 for U.S. Appl. No. 10/525,690.
Office Action dated Dec. 31, 2007 for U.S. Appl. No. 10/579,149.
Office Action dated Jun. 17, 2008 for U.S. Appl. No. 10/579,149.
Office Action dated Dec. 8, 2008 for U.S. Appl. No. 10/579,149.
Office Action dated Jun. 8, 2009 for U.S. Appl. No. 10/579,149.
Press Release—Aug. 23, 2005—"Lorus Indentifies Novel Class of Lead Drug Candidates from Small Molecule Anticancer Program."
Sarshar et al., "Imidazole Libraries on Solid Support," Tetrahedron Lett., vol. 37 (1996) pp. 835-838.
Zeytinoğlu, H. et al., "Mutagenicity Assay in *Salmonella* for Thirteen 2-Substituted-IH-phenanthro (9,10-d) Imidazoles," Dmg and Chemical Toxicology, vol. 26(4) (2003) pp. 245-257.
Buss, J.L. et al., Curr.Top Med. Chern., vol. 4 (15) (2004) pp. 1623-1635.

Chen, C. et al., A possible tumor suppressor role of the KLF5 transcription factor in human breast cancer Oncogene, vol. 21 (2002)pp. 6567-6572.
Chen, J. et al., "Bleomycins: Towards Better Therapeutics" Nat Rev. Cancer, vol. 5(2) (2005) pp. 102-112.
Chen, X., et al. Krüppel-like Factor 4 (Gut-enriched Krüppel-like Factor) Inhibits Cell Proliferation by Blocking $G_1/S$ Progression of Cell Cycle J. Biol. Chern. vol. 276(32) (2001) pp. 30423-30428.
Chao, H. et al., Synthesis, electrochemical and spectroscopic properties of ruthenium(II) complexes containing 1,3-bis([ 1, 10]phenanthroline-[ 5 ,6-d]imidazol-2-yl]benzene, Polyhe-dron, vol. 19(2000) pp. 1975-1983.
Dang, "Overexpression of Krüppel-like factor 4 in the human colon cancer cell line RKO leads to reduced tumorigenecity" D.T. et al., Oncogene, vol. 22(22) (2003).pp. 3424-3430.
Foster, K.W. et al., Increase of GKLF Messenger RNA and Protein Expression during Progression of Breast Cancer Cancer Res., vol. 60(22) (2000) pp. 6488-6495.
Foster, K.W. et al., Cell Growth Differ., vol. 10(6) (1999) pp. 423-434.
Liu, J.G., Enantiomeric ruthenium (II) complexes binding to DNA: binding modes and enantioselectively, JBIC, vol. 27 (2000) pp. 119-128.
Mann, K.J. et al., Biochemistry, vol. 40(5) (2001)pp. 1205-1213.
McCabe, M.J, Jr. et al., Lab. Invest., vol. 69(1)(1993) pp. 101-110.
Xu, H et al., Effects of the ancillary ligands of polypyridyl ruthenium(II) complexes on the DNA-binding behaviors, New J. Chern., vol. 27 (2003) pp. 1255-1263.
Abstract for Nippon Kagaku Zasshi, vol. 92 (1971) pp. 365-370.
Zhang, Q.L, et al, "Design of New Polypyridyl Ligands and Their Effects on DNA-binding Mechanisms of Complexes," Chemical Journal of Chinese Universities, vol. 24(10) (2003) pp. 1753-1755 (Article and Abstract).
Liu et al., "Synthesis, Characterization and Antitumor Activity of a Series of Polypyridyl Complexes" Metal Based drugs, vol. 7(6) (2000) pp. 343-350.
Tanaseichuk et al., "Nitrogen-Containing Heterocyclic Free Radicals, VI. N-Methylindolyldiphenylimidazoles," Chemical Abstracts, vol. 78 (1973) p. 43368.
Alakhov, V. et al., "Block copolymer-based formulation of doxorubicin. From cell screen to clinical trials," Colloids and Surfaces B: Biointerfaces, vol. 16 (1999) pp. 113-134.
Allen, C. et al., "Controlling the physical behavior and biological performance ofliposome formulations through use of surface grafted poly(ethylene glycol)," Biosciences Reports, vo\. 22(20 (2002) pp. 225-250.
Allen, T.M. et al., "Stealth liposomes: an improved sustained release system for 1-beta-D-arabinofuranosylcytosine," Cancer Res., vol. 52 (1992) pp. 2431-2439.
Al-Sarraj, A. et al., "Specificity of transcriptional regulation by the zinc fmger transcription factors Sp1, Sp3, and Egr-1," J Cell Biochem., vol. 94(1) (2005) pp. 153-167.
Andrews, G.K., "Cellular zinc sensors: MTF-1 regulation of gene expression," Biometals, vol. 14 (2001) pp. 223-237.
Bertram et al., "FKBP12-Rapamycin-associated Protein or Mammalian Target of Rapamycin (FRAP/mTOR) Localization in the Endoplasmic Reticulum and the Golgi Apparatus," J. Bioi. Chem., vol. 279(1)(Jan. 2, 2004) pp. 772-778.
Bian, Z. et al., "Syntheses, spectroscopic and c1ystal stmctual stndies of novel imidazo[4,5-f]1,10-phenanthroline derivatives and their Eu(III) tenary complexes with dibenzoylmethane," Polyhedron, vol. 21 (2002) pp. 313-319.
Bian, et al., "The Convenient Synthesis of Amphiphilic Phenanthroline Derivatives," Synthetic Communications, vol. 33(20) (2003) pp. 3477-3482.
Bing et al., "Synthesis of efficient blue and red light emitting phenanthroline derivatives containing both hole and electron transporting properties," Tetrahedron Letters, vol. 45(33) (2004)pp. 6361-6363.
Boyd, M.R. et al., "Data Display and Analysis Strategies for the NCI Disease-Oriented In Vitro Antitumor Dmg Screen," in Cytotoxic Anticancer Dmgs: Models and Discovery and Development, Klimar Academic, Hingham, MA (1992) pp. 11-34.

(56) References Cited

OTHER PUBLICATIONS

Cairo, G. et al., "Induction of Ferritin Synthesis by Oxidative Stress," J. Bioi. Chem., vol. 270(2) (1995) pp. 700-703.
Cammack et al., "EPR Spectroscopy of Iron," Methods Enzymol., vol. 227, Academic Press, Inc. (1993) pp. 353-384.
Cantley, L.C., "The phosphoinositide 3-kinase pathway," Science, vol. 296 (May 31, 2002) pp. 1655-1657.
Chao, H. et al., "Mono-,di-and tetra-nuclear ruthenium(II) complexes containing 2,2'-phenylenebis(imidazo[4,5-t]phenanthroline): synthesis, characterization and third-order non-linear optical properties," J. Chem Soc., Dalton Trans., vol. 12 (2001) pp. 1920-1926.
Chen, J.L. et al. "Gut-enriched Krüppel-like factor represses cyclin D1 promoter activity through Sp1 motif," Nucleic Acids Research, vol. 28(15) (2000) pp. 2969-2976.
Chen, Z.Y et al., "Gut-eriched Krüppel-like Factor Represses Omithine Decarboxylase Gene Expression and Functions as Checkpoint Regulator in Colonic Cancer Cells," J. Bioi. Chem., vol. 227(48) (Nov. 29, 2002) pp. 46831-46839.
Chen, X. et al., "Transcriptional Profiling of Krüppel-like Factor 4 Reveals a Function in Cell Cycle Regulation and Epithelial Differention," J. Mol. Bioi., vol. 326(3) (2003) pp. 665-677.
Chen, S.F. et al., "Selective Inhibition of Dihydroorotate (DHO-DHase) by Brequinar Sodium," Proc. Am. Assoc. Cancer Res., vol. 31 (1990) p. A2644.
Chen et al., "Kruppel-like factor 4 is transactivated by butyrate in colon cancer cells," J. Nutr., vol. 134(4) (2004) pp. 792-798.
Cohen, S.R. et al, "The McGill Quality of Life Questionnaire: a measure of quality of life appropriate for people with advanced disease. A preliminary stndy of validity and acceptability," Palliative Medicine, vol. 9 (1995) pp. 207-219.
Coyle-Rink, J. et al., "Developmental Expression of Wnt Signaling Factors in Mouse Brain," Cancer Biology & Therapy, vol. 1(6) (2002) pp. 640-645.
Crosasso, P. et al., "Preparation, characaterization and properties of sterically stabilized paclitaxel-containing liposomes," J. Controlled Release, vol. 63 (2000) pp. 19-30.
Dang, D. T. et al., "Expression of the gut-enriched Krüppel-like factor (Krüppel-like factor 4) gene in the human colon cancer cell line RKO is dependent on CDX2," Oncogene, vol. 20(35) (2001) pp. 4884-4890.
Dang, D.T. et al., "Opposing effects of Krüppel-like factor 4 (gut enriched Krüppel-like factor) and Krüppel-like factor 5 (intestinal-enriched Krüppel-like factor) on the promoter of the Krüppel-like factor 4 gene," Nucleic Acids Res., vol. 30(13) (2002) pp. 2736-2741.
Dos Santos, L.D. et al., "Improved retention of idarubicin after intravenous injection obtained for cholesterol-free liposomes," Biochim Biophys. Acta., vol. 1561 (2002) pp. 188-201.
Dos Santos, K.A. et aL "pH gradient loading of anthracyclines into cholesterol-free liposomes: enhancing drug loading rates through use of ethanol," Biochim. Biophys. Acta, vol. 1661 (2004) pp. 47-60.
Drummond, C. et aL "Optimizing liposomes for delive1y of chemotherapeutic agents to solid tumors," Pharmacological Reviews, vol. 51(4) (1999) pp. 691-743.
Eisenstein, R.S. et al., "Iron Regulatory Proteins, Iron Responsive Elements nd Iron Homeostasisi[1,2]," J. Nutr., vol. 128(12) (1998) pp. 2295-2298.
Embree, L. et al., "Pharmacokinetic behavior of vincristine sulfate following administration of vincristine sulfate liposome injection," Cancer Chemothr. Pharmacal., vol. 41 (1998) pp. 347-352.
Fields, R.D. et al, "Dual-attribute continuous monitoring of cell proliferation/cytotoxicity," Am. Biotechnol. Lab., vol. 11 (1993) pp. 48-50.
File, T.M., Jr. et aL "Antimicrobial therapy of community-acquired pneumonia," Infect. Dis. Clin. North Am, vol. 18 (2004) pp. 993-1016.
Flatmark, T. et al., "Mitochondrial 'Non-Heme Non-FeS Iron' and It's Significance in the Cellular Metabolism of Iron," Proteins of Iron Metabolism, Brown, Aisen, Fielding and Crichton, eds., New York, Gmn & Stratton (1976) pp. 349-358.

Fruman, D.A. et al., "Phosphoinositide binding domains: embracing 3-phosphate," Cell, vol. 97(7) (1999) pp. 817-820.
Fruman, D.A. et al., "Phosphoinositide kinases," Annu. Rev. Biochem., vol. 67 (1998) pp. 481-507.
Gabizon, A. et al., "Effect of liposome composition and other factors on the targeting of liposomes to experimental tumors: biodistribution and imaging studies," Cancer Res., vol. 50 (1990) pp. 6371-6378.
Gaidenko, T.A. et al., "The PrpC serine threonine phosphatase and PrkC kinase have opposing physiological roles in stationary-phase Bacillus subtilis cells," J. of Bacteriol., vol. 184(22) (2002) pp. 6109-6114.
Gaodeng et al., Chemical Journal of Chinese Universities, vol. 24(10) (2003) pp. 1753-1855).
Gower, J.D. et al., "Determination of Desferrioxamine-Available Iron in Biological Tissues by High-Pressure Liquid Chromatography," Analytical Biochemistry, vol. 180 (1989) pp. 126-130.
Grimmett, M.R., "Imidazoles and their Benzo Derivatives: (iii) Synthesis and Applications, 4.08.1 Ring Synthesis from Non-Heterocyclic Compounds," Comprehensive Heterocyclic Chemisuy: the Structure, Reaction, Synthesis and Uses of Hetrocyclic Compounds, Katrizky and Rees, eds., vol. 5, Pergamon Press, Oxford (1984)pp. 457-498.
Gross, C. et al., "Identification of the Copper Regulon in *Saccharomyces cerevisiae* by DNA Microarrays," J. Biol. Chem., vol. 275(41) (Oct. 13, 2000) pp. 32310-32316.
Hanai, T. et al., "Prediction of retention factors of phenolic and nitrogen-containing compounds in reversed-phase liquid chromatography based on logP and pKa obtained by computational chemical calculation," Journal of Liquid Chromatography & Related Technologies, vol. 23(3) (2000) pp. 363-385.
Haroon, Z.A. et al., "Loss of metal transcription factor-1 suppresses tnmor growth through enhanced matrix deposition," Faseb J., vol. 18(11)(2004)pp. 1176-1184.
Hiort, C. et al., "DNA Binding of /1,.-and A.-[Ru(phen)2DPPZf+," J. Am. Chem. Soc., vol. 115 (1993)pp. 3448-3454.
Hollingshead, M. et al., "In Vivo Cultivation of Tumor Cells in Hollow Fibers," Life Sciences, vol. 57)2) (1995) pp. 131-141.
Hong, X. et al., "Synthesis and spectroscopic RNA binding studies of [Ru(phenhMHPIPf+," Inorg. Chem. Commun., vol. 6(2003) pp. 766-768.
Hong, X. et al., "Effects of ligand planitary on the interaction of polypyridyl Ru(II) complexes with DNA," J. Royal Society of Chemistry., Dalton Trans., vol. 11 (2003) pp. 2260-2268.
Janoff, A.S., "Liposomal delivery of drugs, genes and vaccines," Liposomes: Rational Design, Biotechnology Advances, vol. 17 (1999) pp. 511-513.
Kihara, A. et al., "Beclin-phosphatidylinositol 3-kinase complex functions at the trans-Golgi network," EMBO Rep., vol. 2(4) (200 1) pp. 330-335.
King, F.G. et al., "Physiological pharmacokinetic parameters for Cis-Dichlorodiammineplatimun(II) (DDP) in the mouse," J. Pharmacokinet. Biophar., vol. 20 (1) (1992) pp. 95-99.
Kitano, Y. et al., "Suppression of proliferation of human epidermal keratinocytes by 1,25-dihydroxyvitamin $D_3$," Euro J. Clin. Investg., vol. 21 (1991) pp. 53-58.
Kozlov, A.V. et al., "Intracellular Free Iron in Liver Tissue and Liver Homogenate: Studies with Electron Pa Tarnagnetic Resonance on the Formation of Paramagnetic Complexes with Desferal and Nitric Oxide," Free Radic. Bioi. Med., vol. 13 (1992) pp. 9-16.
Langmade, S.J. et al., "The Transcription Factor MTF-1 Mediates Metal Regulation of the Mouse ZnTI gene," J. Bioi Chem., vol. 275(44) (Nov. 3, 2000) pp. 34803-34809.
Lichtlen, P. et al., "Putting its fingers on stressful situations: the heavy metal-regulatory transcription factor MTF-1," Bioessays, vol. 23(11)(2001) pp. 1010-1017.
Liggins, R.T. et al., "Solid-state characterization of paclitaxel," J. Pharm. Sci, vol. 86)12) (Dec. 12, 1997) pp. 1458-1563.
Linden P.K., "Treatment options for vancomycin-resistant enterococcal infections," Drugs, vol. 62 (2002) pp. 425-441.
Liu, J. et al., "Influence of serum protein on polycarbonate-based copolymer micelles as a delivery system for a hydrophobic anti-cancer agent," J. Controlled Release, vol. 103 (2005) pp. 481-497.

(56) References Cited

OTHER PUBLICATIONS

Liu, J. et al., "Polymer-drug compatibility: a guide to the development of delivery systems for the anticancer agent, ellipticine," J. Phann. Sci., vol. 93(1) (2004) pp. 132-143.
Lockshin, R.A. et al., "Apoptosis, autophagy and more," Int. J. Biochem. Cell Bioi., vol. 36(12) (2004) pp. 2405-2419.
Lowy, F.D., *Staphylococcus aures* infections, N. Engl. J. Med, vol. 339(8) (1998) pp. 520-532.
Lukyanov, A.N. et al., "Polythylene glycol-diacyllipid micelles demonstrate increased acctunulation in subcutaneous tumors, in mice," Phar. Res., vol. 19(10) (2002) pp. 1424-1429.
Martini, L.A. et al., "Iron Treatment Downregulates DMTI and IREG1 mRNA.Expression in Caco-2 cells," J. Nutr., vol. 132(4) (2002) pp. 693-696.
McCorkle, R. et al., "Development of a system distress scale" Cancer Nursing, vol. 1 (1978) pp. 373-378.
Meijer, A.J. et al., "Regulation and role of autophagy in mmnmalian cells," Int. J.Biochem. Cell Biol., vol. 36(12) (2004) pp. 2445-2462.
Moghimi, S.M. et al., "Real-time evidence of surface modification at polystyrene lattices by poloxamine 908 in the presence of serum: in vivo conversion of macrophage-prone nanoparticles to stealth entities by poloxamine 908," FEBS. Lett., vol. 547 (2003) pp. 177-182.
Monks, A. et al., "Feasibility of a High-flux Anticancer Drug Screen Using a Diverse.Panel of Cultured Hwnan Tumor Cell Lines," J. Natl. Cancer Inst., vol. 83(11)(Jun. 5, 1991)pp. 757-766.
Moribe, K. et al., "Encapsulation characteristics of nystatin in liposomes: effects of cholesterol and polyethylene glycol derivatives," International Journal of Pharmaceutics, vol. 188 (1999), pp. 193-202.
Mizumura, Y. et al., "Cisplatin-incorporated polymeric micelles eliminate.nephrotoxicity, while maintaining antitumor activity," Japanese Journal of Cancer Research, vol. 92 (2001) pp. 328-336.
Nielson, P. et al., "Non-Transferrin-BoWid-Iron in Serum and Low-Molecular-Weight-Iron in the Liver of Sietary Iron-Loaded Rats," in. J. Biochem., vol. 25(2) (1993) pp. 223-232.
O'Brien, J. et al., "Investigation of the Alamar Blue (resazurin) fluorescent dye for the assessment of mammalian cell cytotoxicity," Eur. J. Biochem., vol. 267 (2000) pp. 5421-5426.
Office Action dated Nov. 18, 2009 for U.S. Appl. No. 10/525,690.
Office Action dated Dec. 14, 2009 for U.S. Appl. No. 10/525,690.
Office Action dated Jun. 4, 2010 for U.S. Appl. No. 10/525,690.
Notice of Allowance dated Aug. 26, 2010 for U.S. Appl. No. 10/525,690.
Office Action dated Jan. 28, 2008 for U.S. Appl. No. 10/579,149.
Office Action dated Jan. 8, 2010 for U.S. Appl. No. 10/579,149.
Office Action dated Oct. 29, 2010 for U.S. Appl. No. 10/579,149.
Patel, R., "Clinical impact of vancomycin-resistant enterococci," J. Antimicrob. Chemother., vol. 51(Suppl. S3) (2003) pp. 13-21.
Öllinger, K. et al., "Nutrient Deprivation of Cultured Rat Hepatocytes Increases the Desferrioxmnine-available Iron Pool and Augments the Sensitivity to Hydrogen Peroxide," J. Biol. Chem. vol. 272(38) (1997)pp. 23707-23711.
Patel, H.M. et al., "Serum-mediated recognition of liposomes by phagocytic cells of the reticuloedothelial system—The concept of tissue specificity," Adv. Dmg Deliv. Rev., vol. 32 (1998) pp. 45-60.
Petrat, F. et al., "The Chelatable Iron Pool in Living Cells: A Methodically Defined Quantity," Biol.Chem., vol. 383(3-4) (2002) pp. 489-502.
Rameh, L.E. et al., "The role of phosphoinositide 3-kinase lipid products in cell function," J. Biol. Chem., vol. 274(13) (1999) pp. 8347-8350.
Rubinstein, L.V. et al., "Comparison of in Vitro Anticancer-Drug-Screening Data Generated with a Tetrazolium Assay Versus a Protein Assay Against a Diverse Panel of Human Tumor Cell Lines," J. Natl. Cancer Inst., vol. 82 (1990)pp. 1113-1118.
Sakurai, Y. et al., "Development of the polymer micelle carrier system for doxombicin," J. Controlled Release, vol. 74 (2001) pp. 295-302.
Scialli, R. et al., "Protective effects of liposome encapsulation on paclitaxel development toxicity in the rat," Teratology, vol. 56 (1997) pp. 305-310.
Sharma, E. et al., "Activity of paclita-xel liposome formulations against human ovarian tumor xenografts," Int. J. Cancer, vol. 71 (1997) pp. 103-107.
Sherr, C.J. et al., "Inhibitors of marnnalian G1 cyclin-dependent kinases,"Genes and Development, vol. 9(10)(1995)pp. 1149-1163.
Shie, J.L. et al., "Gut-enriched Kruppel-like factor represses cyclin D1 promoter activity through Sp1 motif," Nucleic Acids Res., vol. 28(15) (2000) pp. 2969-2976.
Shie, J.L. et al., "Role of gut-enriched Kruppel-like factor in colonic cell growth and differentiation," A. J. Physiol. Gastrointest. Liver PhysioL, vol. 279(4) (2000) pp. G806-G814.
Shields, J.M. et al., "Identification and Characterization of a Gene Encoding a Gut-enriched Kruppel-like Factor Expressed during Growth Arrest," The Journal of Biological Chemistry, vol. 271(33) (1996) pp. 20009-20017.
Siegel, T. et al., "Doxombicin encapsulated in sterically stabilized liposomes for the treatment of a brain tumor model: biodistribution and therapeutic efficacy," J. Neurosurg., vol. 83 (1995) pp. 1029-1037.
Skehan, P. et al., "New Colorimetric Cytotoxicity Assay for Screening," J. Natl. Cancer Inst., vol. 82 (1990)pp. 1107-1112.
Tardi, P.G. et al., "Iposomal doxorubicin," J. Drug Targeting, vol. 4(3) (1996) pp. 129-140.
Torchilin, V.P. et al., "Immtmomicelles: Targeted pharmaceutical carriers for poorly soluble drugs," Proc. Natl. Acad. Sci., USA, vol. 100 (2003) pp. 6039-6044.
Vanhaesebroeck, B. et al., "Signaling by distinct classes of phosphoinositide 3-kinases," Exp. Cell Res., vol. 253(1) (1999) pp. 239-254.
Vassilev, LT. et al., "Cell-based screening approach for anti tumor drug leads which exploits sensitivity differences between normal and cancer cells: identification of two novel cell-cycle inhibitors," Anti-Cancer Drug Design, vol. 16 (200 1) pp. 7-17.
West, M.R. et al, "Simple Assays of Retinoid Activity as Potential Screens for Compounds That May Be Useful in Treatment of Psoriasis," J. Investigative Derm., vol. 99 (1992) pp. 95-100.
Yamada, M. et al., "Synthesis of 2,9-Dichloro-1,10-phenanthroline from N,N'-Annelated Phenanthrolinediones," Bull. Soc. Chem. Jpn., vol. 63(9) (1990) pp. 2710-2712.
Yamamoto, Y. et al., "Long-circulating poly(ethylene glycol)-poly(D,L-lactide) block copolymer micelles with modulated surface charge," J. Controlled Release, vol. 77 (2001) pp. 27-38.
Yegorov, D.Y. et al., "Simultaneous Determination of Fe(III) and Fe(II) in Water Solutions and Tissue Homogenates Using Desferal and 1,10-Phenanthrolin," Free Radic. Biol. Med., vol. 15 (1993) pp. 565-574.
Yokoyama, M. et al., "Characterization of physical entrapment and chemicalconjugation of adriamycin in polymeric micelles and their design for in vivo delivery to a solid tumor," J. of Controlled Release, vol. 50 (1998) pp. 79-92.
Zalewski, P.D. et al., "Correlation of apoptosis with change in intracellular labile Zn(II) using Zinquin [(2-methyl-8-p-toluenesulphonamido-6-quinolyloxy)acetic acid], anew specific fluorescent probe for Zn(II)," Biochem. J., vol. 296(Pt. 2) (1993) pp. 403-408.
Zhang, C., "Bacterial signaling involving eukaryotic-type protein kinases," Mol Microb., vol. 20(1) (1996) pp. 9-15.
Zhang, J.A. et al., "Development and characterization of a novel Cremophor® EL free liposome-based paclitaxel (LEP-ETU) formulation," Eur. J. Pharm. Biophar., vol. 59 (2005) pp. 177-187.
Zhang, W. et al., "The gut-eniched Kruppel-like factor(Kruppel-like factor 4) mediates the transactivating effect of p53 on the $p21^{WAF1/Cip1}$ promoter," J. Biol. Chem., vol. 275 (24) (2000) pp. 18391-18398.
Zhao, W. et al., "Identification of Kruppel-like factor 4 as a potential tumor suppressor gene in colorectal cancer," Oncogene, vol. 23(2) (2004) pp. 395-402.
Zhuang, H. et al., Synthesis and character of two new Nl-phenanthroline flue-rescence probe for nucleic acid determination, College of Enviromnent Science and Engineering, Huaxue Shiji, vol. 25(6) (2003) pp. 325-328 (Abstract).

(56) References Cited

OTHER PUBLICATIONS

Yun-Jun Liu et al. "Synthesis, Structure, DNA-Binding Properties, and Cytot oxicity of Ruthenium(II) Polypridyl Complexes", Chemistry & Biodiversity, 2010, vol. 7, No. 7, pp. 1770-1783.
International Search Report and Written Opinion, mailed Sep. 26, 2014, for International Application No. PCT/US2014/031349.
International Preliminary Report on Patentability, mailed Oct. 1, 2015, for International Application No. PCT/US2014/031349.
Antolini et al. "Analogues of 4, 5-bis(3, 5-Dichlorophenyl-2-Trifluoromet-hyl-1H-Imidazole as Potential Antibacterial Agents" Bioorganic & Medicinal Chemistry Letters, Oxford, GB, vol. 9, No. 7, Apr. 5, 1999, pp. 1023-1028.
International Search Report, mailed Feb. 26, 2004, for International Application No. PCT/CA03/01229.
Written Opinion, mailed May 24, 2004, for International Application No. PCT/CA03/01229.
Written Opinion, mailed Jun. 21, 2004, for International Application No. PCT/CA03/01229.
International Preliminary Examination Report, mailed Dec. 3, 2004, for International Application No. PCT/CA03/01229.
Database Excerpts for Molecular Formulas, STN Easy, Sep. 11, 2009.
Database Excerpt for Molecular Formula C23 H16 N4O2, AsInEx, Nov. 10, 2009.
Database Excerpt for Molecular Formula C23 H12 Br I2 N3, Chembridge Corp., Nov. 10, 2009.
Dora, E.K. et al. Synthesis of Some Fused 2-Arylimidazoles and their Derivatives, J. Indian Chem. Soc., Jun. 1979, vol. 56, No. 6, pp. 620-624.
Bhaduri et al. Potential Antifertility Agents: Syntheses of 2,4,5-Substituted Imidazoles, Indian J. Chem., vol. 4 (9), Sep. 1966, 419-420.
Pechkin, A.A. et al., Synthesis and Properties of 2-(2-Furyl)-and 2-(2-Thienyl)-1-methylphenanthro[9,10-d]imidazoles, Russian Journal of Organic Chemistry (Translation of Zhurnal Organicheskoi Khimii), 2002, vol. 38, No. 5, p. 726-730.
Pozharskii, F.T. et al. "Synthesis and Transformations of 2-(2-FURYL)-and 2-[β-(2-FURYL)VINYL] Phenanthr [9,10] Imidazoles" S. Chem. Het. Comp. 1971, 7, 950-952.
Roshal, A.D. et al. "The Electronic Transitions and Spectra of Hetarylphenanthroimidazole Derivatives," Russ. J. Phys. Chem. 2003, 77, 1709-1714.
Sircar et al. "Dyes Derived from Phenanthraquinone. Part III. Phenanthriminazoles." J. Chem. Soc. 1923, 123, 1559-1565.
Steck et al."Reactions ofPhenathraquinone and Retenequinone with Aldehydes and Ammonium Acetate in Acetic Acid Solution," J. Am. Chem. Soc., 65:452-456 (1943).
Ito, Yoshikatsu et al. "Photochemical Reaction of Imidazoles with Unsaturated Nitriles. Chemistry of Encounter Complex and Ion Pair" J. Org. Chem. 1979, vol. 44, No. 1, pp. 41-49.
Isikdag et al. "Synthesis and analgesic activities of 2-substituted-1H-phenantro [9,10-d] imidazoles" Boll. Chim. Farmaceutico 1999, 138, 453-456.
Lantos, "Reaction of Phenanthrenequinone with Ammonium Acetate," J. Org. Chem., 40(11) 1641-1642 (1975).
International Search Report and Written Opinion, mailed Apr. 4, 2005 for International Application No. PCT/IB2004/052433.
International Preliminary Report on Patentability, issued May 15, 2006 for International Application No. PCT/IB2004/052433.
Medicines in Development for Infectious Diseases 2010, "Biopharmaceutical Research Continues Against Infectious Diseases with 395 Medicines and Vaccines in Testing," 36 pages.
International Search Report and Written Opinion, mailed Jan. 3, 2007 for International Application No. PCT/IB2006/051675.
International Preliminary Report on Patentability, issued Nov. 29, 2007, for International Application No. PCT/IB2006/051675.

* cited by examiner

2-SUBSTITUTED IMIDAZO[4,5-D]PHENANTHROLINE DERIVATIVES AND THEIR USE IN THE TREATMENT OF CANCER

CROSS-REFERENCE TO RELATED APPLICATION

This application is a U.S. national stage application under 35 U.S.C. §371 of International Application No. PCT/US2014/031349, filed on Mar. 20, 2014, which claims the benefit of priority to U.S. Provisional Application No. 61/803,627, filed on Mar. 20, 2013, the contents of each of which are hereby incorporated by reference in their entireties for all purposes

FIELD OF INVENTION

This invention pertains to the field of anti-cancer compounds and, in particular, to the use of therapeutically active 2-substituted imidazo[4,5-d]phenanthroline derivatives in the treatment of cancer.

BACKGROUND OF THE INVENTION

A cancer is a malignant tumour of potentially unlimited growth. It is primarily the pathogenic replication (a loss of normal regulatory control) of various given types of cells found in the human body. By select mutation resulting from a primary lesion, the DNA of a cancer cell evolves and converts the cell into an autonomous system.

Conventional cancer treatments have focused mainly on killing cancerous cells. Chemotherapeutic agents currently used for anti-cancer/anti-tumour therapy are selected for their toxicity towards rapidly proliferating cells. Most of them cause undesirable systemic effects such as cardiac or renal toxicity, marrow aplasia, alopecia, nausea and vomiting. During the last few years, many researchers have tried to eliminate these side effects by developing drugs having suitable physico-chemical properties allowing an increase of the availability of the drug to the tumour site. New molecules extracted from natural sources, synthetically or semi-synthetically produced, enzymes, radioisotopes, DNA toxins, various macromolecules, and antibodies against fibrin or against tumour-specific surface antigens are bound to drugs in an attempt to increase selectivity of the chemotherapeutic agents.

The effectiveness of most anticancer agents is greatly reduced because of their high toxicity and the nature of the illness. It is believed that the problem of high toxicity of the anticancer agents can be circumvented by chemical modifications of those structures in such a way that they act more specifically on tumour cells without increasing systemic toxicity. The research in this field is therefore mainly directed to the synthesis of anticancer agents which would possess high antineoplastic activity, low systemic toxicity and low mutagenicity on normal cells.

Heterocyclic compounds, especially heterocyclic azole derivatives, have been shown to have a wide spectrum of biological activities. One class of compounds with interesting biological activities is the imidazoles (derivatives containing a five-membered heterocyclic azole). A variety of biological activities have been reported for imidazole derivatives with different substitution patterns (Lee et al. Nature 1994 327: 739-745; Abdel-Meguid et al. *Biochemistry*, 1994, 33:11671; Heerding et al. *Bioorg. Med. Chem. Lett.* 2001, 11:2061-2065; Bu et al. *Tetrahedron Lett.* 1996, 37:7331-7334; Lewis J R. *Nat. Prod. Rep.* 1999, 16:389-418; Lewis J R. *Nat. Prod. Rep.* 1998, 15:417-437 and 371-395).

Biological activities have also been reported for aryl-imidazole derivatives, for example, these compounds can act as modulators of multi-drug resistance in cancer cells (Zhang et al. *Bioorg. Med. Chem. Lett.* 2000, 10:2603-2605), inhibitors of p38 MAP kinase (Adams et al. *Bioorg. Med. Chem. Lett.* 2001, 11:867-2870, McLay et. al. *Bioorg. Med. Chem.* 2001, 9:537-554) and of cytokines (U.S. Pat. Nos. 5,656,644; 5,686,455; 5,916,891; 5,945,418; and 6,268,370), and inhibitors of bacterial growth (Antolini et al. *Bioorg. Med. Chem. Lett.* 1999, 9:1023-1028). A few reports have indicated that triarylimidazole compounds can act as inhibitors of p38 MAP kinase (for example, see LoGrasso et al. *Biochemistry.* 1997, 36:10422-10427) and as modulators of multi-drug resistance in cancer cells (Sarshar et al. *Bioorg. Med. Chem. Lett.* 2000, 10:2599-2601), however, the majority of the literature indicates that these compounds have found use mainly as colour producing reagents (U.S. Pat. Nos. 4,089,747; 5,024,935; 5,047,318; 5,496,702; 5,514,550; and 5,693,589) and as photopolymerization initiators (U.S. Pat. Nos. 6,117,609 and 6,060,216), generally in dimeric form.

The potential anti-cancer activity of a number of compounds has been investigated by the National Cancer Institute (NCI), which has undertaken a large scale screening of several thousand compounds to try to identify those that have potential therapeutic application in the treatment of cancer (NCI Yeast Anticancer Drug Screen). The screen is based on the ability of candidate compounds to inhibit the growth of *Saccharmyces cerevisiae* strains that have mutations in genes related to cell cycle control and DNA repair damage. Compounds are initially screened against a panel of six yeast strains at a single concentration (Stage0). Compounds with activity in Stage0 are re-screened against the same panel at two concentrations (Stage1). Selected compounds with activity in Stage1 that also show selectivity are re-screened against a panel of 13 yeast strains at five concentrations (Stage2). Many of the results from the screening have been made available on the NCI/DTP website. The approach adopted in this screen is dependent on a candidate compound exerting its activity on certain cellular pathways (i.e. cell cycle control or DNA repair damage). The results generated by this type of screen, therefore, represent a very preliminary stage of screening for potential anti-cancer drugs and do not necessarily correlate with the ability of a compound to inhibit the growth of cancer cells in vitro or in vivo.

The NCI also provides an in vivo screening program to try to identify potential anti-cancer drugs (NCI In Vivo Anticancer Drug Screen). Many of the results from this screening program are also available from the NCI/DTP website.

Amongst those compounds tested in one or both of the NCI screens are some aryl imidazole compounds (NCI #322334, 338970, 144033). None of these three compounds showed any activity in the In Vivo Anticancer Drug Screen, even though one of these compounds (NCI #338970) had been reported as active in Stage0 testing in the Yeast Anticancer Drug Screen. The fact that this compound was active in the yeast screen yet showed no activity in the in vivo assay confirms that a positive result in the yeast screen is not necessarily predictive of the utility of a compound as in anticancer therapeutic.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

It is an object of the present invention to provide a class of compounds which are 2-substituted imidazo[4,5-d]phenanthroline derivatives that have anti-cancer activity. In accordance with an aspect of the present invention, there is provided a compound having structural formula (I), or a salt or solvate thereof, as an anti-cancer agent:

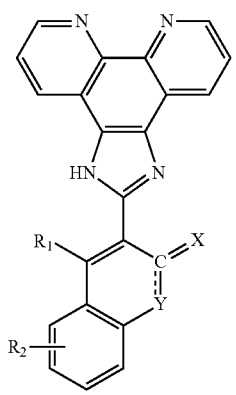

(I)

or a salt or solvate thereof, wherein:
- - - - between C and X, and between C and Y designates a single or a double bond, and at least one of - - - is a single bond;
X is optionally substituted alkoxy or $NR_3R_4$ when - - - between C and X is single bond, or
X is O when - - - between C and X is a double bond;
Y is N when - - - between C and Y is a double bond, or Y is NH, when - - - between C and Y is a single bond;
$R_1$ and $R_2$ are independently H, optionally substituted alkyl, or optionally substituted alkoxy, and
$R_3$ and $R_4$ are taken together to form a 5 or 6 membered optionally substituted heterocycle, having at least one heteroatom that is N or O; and
provided that when X is O and - - - between C and X is a double bond; then $R_1$ and $R_2$ both are not H.

In accordance with another aspect of the present invention, there is provided a use of a compound having structural formula (I), or a salt or solvate thereof, in the preparation of an anti-cancer composition. In some embodiments, the compounds are useful for lymphoma treatment.

In accordance with another aspect of the present invention, there is provided a compound having the structural formula:

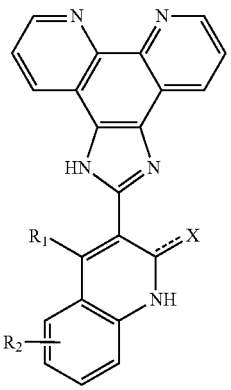

(II)

or a salt or solvate thereof, wherein:
- - - designates a single or a double bond;
X is optionally substituted alkoxy or $NR_3R_4$ when - - - is single bond, or
X is O when - - - is a double bond;
$R_1$ and $R_2$ are independently H, optionally substituted alkyl, or optionally substituted alkoxy; and
$R_3$ and $R_4$ are taken together to form a 5 or 6 membered optionally substituted heterocycle, having at least one heteroatom that is N or O; and
provided that when X is O and - - - between C and X is a double bond; then $R_1$ and $R_2$ both are not H.

In accordance with another aspect of the present invention, there is provided use of a compound having structural formula (II), or a salt or solvate thereof, in the preparation of an anti-cancer composition. In some embodiments, the compounds are useful for lymphoma treatment.

In accordance with another aspect of the present invention, there is provided a compound having the structural formula:

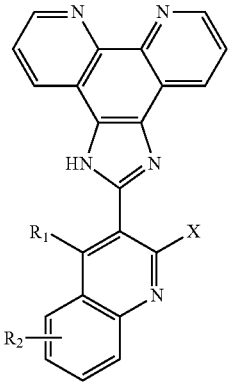

(III)

or a salt or solvate thereof, wherein:
X is optionally substituted alkoxy or $NR_3R_4$;
$R_1$ and $R_2$ are independently H, optionally substituted alkyl, or optionally substituted alkoxy; and
$R_3$ and $R_4$ are taken together to form a 5 or 6 membered optionally substituted heterocycle, having at least one heteroatom that is N or O.

In accordance with another aspect of the present invention, there is provided use of a compound having structural formula (III), or a salt or solvate thereof, in the preparation of an anti-cancer composition. In some embodiments, the compounds are useful for lymphoma treatment.

In accordance with another aspect of the present invention, there is provided a compound having the structural formula:

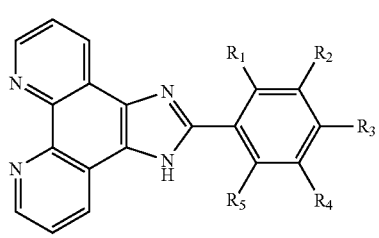

(IV)

or a salt or solvate thereof, wherein:
one of $R_1$ and $R_2$, or $R_2$ and $R_3$, or $R_3$ and $R_4$, or $R_4$ and $R_5$, when taken together with the carbon atoms, to which they are attached form a 5 or 6 membered optionally substituted heterocycle, having at least one heteroatom that is N or O,
and remaining of R1 to R5 are independently H, optionally substituted alkyl, or optionally substituted alkoxy.

In accordance with another aspect of the present invention, there is provided a use of a compound having structural formula (IV), or a salt or solvate thereof, in the preparation of an In anti-cancer composition. In some embodiments, the compounds are useful for lymphoma treatment.

DETAILED DESCRIPTION OF THE INVENTION

Figure 1:
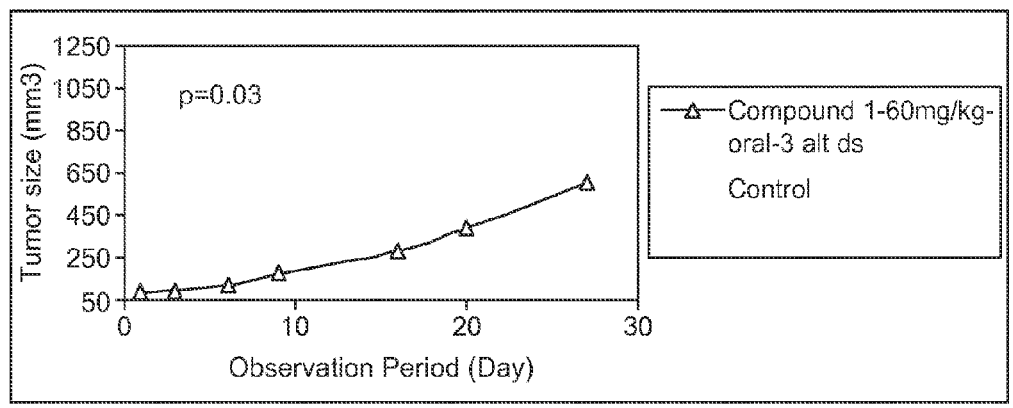
FIG. 1 depicts in vivo efficacy of compound 1 in a colon carcinoma (HT-29) xenograft model.

The present invention provides a class of 2-substituted imidazo[4,5-d]phenanthroline imidazole compounds and for their use as anti-cancer agents. The present invention further provides for methods of inhibiting neoplastic cell growth and/or proliferation in an animal by administering to the animal an effective amount of a compound of Formula I, either alone or in combination with one or more standard chemotherapeutics.

Definitions

Unless defined otherwise, all technical and scientific terms used herein have the same meaning as commonly understood by one of ordinary skill in the art to which this invention pertains.

The terms "a" and "an" do not denote a limitation of quantity, but rather denote the presence of at least one of the referenced item. The term "or" or "and/or" is used as a function word to indicate that two words or expressions are to be taken together or individually. The terms "comprising", "having", "including", and "containing" are to be construed as open-ended terms (i.e., meaning "including, but not limited to"). The endpoints of all ranges directed to the same component or property are inclusive and independently combinable.

The terms are defined as follows: The term "halogen" refers to fluorine, bromine, chlorine, and iodine atoms.

"Alkyl," by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. The term "alkyl" includes "cycloalkyl" as defined herein below. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In some embodiments, an alkyl group comprises from 1 to 20 carbon atoms ($C_1$-$C_{20}$ alkyl). In other embodiments, an alkyl group comprises from 1 to 10 carbon atoms ($C_1$-$C_{10}$ alkyl). In still other embodiments, an alkyl group comprises from 1 to 6 carbon atoms ($C_1$-$C_6$ alkyl) or 1 to 4 carbon atoms ($C_1$-$C_4$ alkyl). $C_1$-$C_6$ alkyl is also known as "lower alkyl".

The term "alkoxy" refers to the group —OR, where R is alkyl or substituted alkyl as defined herein.

"Amine" refers to a moiety having structural formula of —$NH_2$. "Substituted amine" refers to a moiety having structural formula of —$NR^XR^Y$, wherein $R^X$ and $R^Y$ are independently hydrogen (provided that $R^X$ and $R^Y$ are not both hydrogen), alkyl, substituted alkyl, heteroalkyl, substituted heteroalkyl, aryl, substituted aryl, arylalkyl, substituted arylalkyl, heteroaryl, substituted heteroaryl, heteroarylalkyl, substituted heteroarylalkyl, carbocyclyl, substituted carbocyclyl, heterocyclyl, substituted heterocyclyl, acyl, substituted acyl, imine, substituted imine, amidine, e.g., —C(NH)—$NH_2$, or substituted amidine. In some embodiments of —$NR^XR^Y$, $R^X$ is hydrogen, and $R^Y$ is alkyl, substituted alkyl, heteroalkyl, substituted heteroalkyl, aryl, substituted aryl, arylalkyl, substituted arylalkyl, heteroaryl, substituted heteroaryl, heteroarylalkyl, substituted heteroarylalkyl, carbocyclyl, substituted carbocyclyl, heterocyclyl, substituted heterocyclyl, acyl, substituted acyl, imine, substituted imine, amidine, e.g., —C(NH)—NH$_2$, or substituted amidine.

"Halo," by itself or as part of another substituent refers to a radical —F, —Cl, —Br or —I.

"Salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Solvate" means a compound formed by solvation (the combination of solvent molecules with molecules or ions of the solute), or an aggregate that consists of a solute ion or molecule, i.e., a compound of the present invention, with one or more solvent molecules. When water is the solvent, the corresponding solvate is "hydrate".

"Substituted," when used to modify a specified group or radical, means that one or more hydrogen atoms of the specified group or radical are each, independently of one another, replaced with the same or different substituent(s). The term "optionally substituted" means substitued or nonsubstituted (i.e., unsubstituted). For example, an optionally substituted azacyclic ring means the azacyclic ring can be substituted or nonsubstituted. Substituent groups useful for substituting saturated carbon atoms in the specified group or radical include, but are not limited to —R$^a$, halo, —O$^-$, =O, —OR$^b$, —SR$^b$, —S$^-$, =S, =NR$^c$R$^c$, =NR$^b$, =N—OR$^b$, trihalomethyl, —CF$_3$, —CN, —OCN, —SCN, —NO, —NO$_2$, =N$_2$, —N$_3$, —S(O)$_2$R$^b$, —S(O)$_2$NR$^b$, —S(O)$_2$O$^-$, —S(O)$_2$OR$^b$, —OS(O)$_2$R$^b$, —OS(O)$_2$O$^-$, —OS(O)$_2$OR$^b$, —P(O)(O$^-$)$_2$, —P(O)(OR$^b$)(O), —P(O)(OR$^b$)(OR$^b$), —C(O)R$^b$, —C(S)R$^b$, —C(NR$^b$)R$^b$, —C(O)O$^-$, —C(O)OR$^b$, —C(S)OR$^b$, —C(O)NR$^c$R$^c$, —C(NR$^b$)NR$^c$R$^c$, —OC(O)R$^b$, —OC(S)R$^b$, —OC(O)O$^-$, —OC(O)OR$^b$, —OC(S)OR$^b$, —NR$^b$C(O)R$^b$, —NR$^b$C(S)R$^b$, —NR$^b$C(O)O$^-$, —NR$^b$C(O)OR$^b$, —NR$^b$C(S)OR$^b$, —NR$^b$C(O)NR$^c$R$^c$, —NR$^b$C(NR$^b$)R$^b$ and —NR$^b$C(NR$^b$)NR$^c$R$^c$, where R$^a$ is selected from the group consisting of alkyl, cycloalkyl, heteroalkyl, cycloheteroalkyl, aryl, arylalkyl, heteroaryl and heteroarylalkyl; each R$^b$ is independently hydrogen or R$^a$; and each Re is independently R$^b$ or alternatively, the two R$^c$s may be taken together with the nitrogen atom to which they are bonded form a 4-, 5-, 6- or 7-membered cycloheteroalkyl which may optionally include from 1 to 4 of the same or different additional heteroatoms selected from the group consisting of O, N and S. As specific examples, —NR$^c$R$^c$ is meant to include —NH$_2$, —NH-alkyl, N-pyrrolidinyl and N-morpholinyl. As another specific example, a substituted alkyl is meant to include -alkylene-O-alkyl, -alkylene-heteroaryl, -alkylene-cycloheteroalkyl, -alkylene-C(O)OR$^b$, -alkylene-C(O)NR$^b$R$^b$, and —CH$_2$—CH$_2$—C(O)—CH$_3$. The one or more substituent groups, taken together with the atoms to which they are bonded, may form a cyclic ring including cycloalkyl and cycloheteroalkyl.

The above-referenced substituents as represented by chemical formulas are also readily recognized by their chemical names known to one skilled in the art. For example, those substituents include alkyl, heteroalkyl, halo, hydroxyl, alkoxy, amino, alkylamino, cyano, nitro, haloalkyl, carboxylic acid, amide, ester, acyl, thiol, alkylthio, sulfonamide, and etc.

The substituents used to substitute a specified group can be further substituted, typically with one or more of the same or different groups selected from the various groups specified above.

The terms "therapy" and "treatment," as used interchangeably herein, refer to an intervention performed with the intention of alleviating the symptoms associated with, preventing the development of, or altering the pathology of a disease, disorder or condition. Thus, the terms therapy and treatment are used in the broadest sense, and include the prevention (prophylaxis), moderation, management, reduction, or curing of a disease, disorder or condition at various stages. Prevention or reduction of the progression of a disease, disorder or condition are encompassed by these terms. Also encompassed by these terms is an intervention resulting in an alteration of physiology and/or biochemistry of a living subject. Those in need of therapy/treatment include those already having the disease, disorder or condition as well as those prone to, or at risk of developing, the disease, disorder or condition and those in whom the disease, disorder or condition is to be prevented. The therapeutic application of compounds of the invention, therefore, refers to a therapy or treatment, as defined herein.

The terms "subject" or "patient," as used herein, refer to an animal in need of treatment, including humans and other mammals.

Administration of the compounds of the invention "in combination with" one or more further therapeutic agents, is intended to include simultaneous (concurrent) administration and consecutive administration. Consecutive administration is intended to encompass various orders of administration of the therapeutic agent(s) and the compound(s) of the invention to the subject.

The term "adjuvant therapy," as used herein, refers to a treatment that is added to increase the effectiveness of a primary treatment. In cancer, adjuvant therapy usually refers to chemotherapy, hormonal therapy or radiation therapy after surgery (primary therapy) to increase the likelihood of killing all cancer cells.

The term "neoadjuvant therapy," as used herein, refers to a treatment given before the primary treatment. Examples of neoadjuvant therapy include chemotherapy, radiation therapy, and hormone therapy.

As used herein, the term "about" refers to a +/−10% variation from the nominal value. It is to be understood that such a variation is always included in any given value provided herein, whether or not it is specifically referred to.

I. 2-substituted imidazo[4,5-d]phenanthroline Compounds

The present invention provides compounds of the general formula (I):

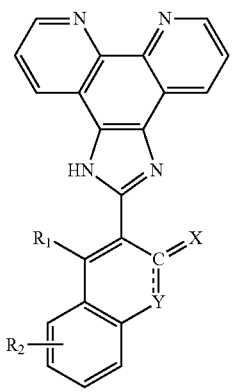

or a salt or solvate thereof, wherein:
- --- between C and X, and between C and Y designates a single or a double bond, and at least one of --- is a single bond;
- X is optionally substituted alkoxy or $NR_3R_4$ when --- between C and X is single bond, or
- X is O when --- between C and X is a double bond;
- Y is N when --- between C and Y is a double bond, or Y is NH, when --- between C and Y is a single bond;
- $R_1$ and $R_2$ are independently H, optionally substituted alkyl, or optionally substituted alkoxy, and
- $R_3$ and $R_4$ are taken together to form a 5 or 6 membered optionally substituted heterocycle, having at least one heteroatom that is N or O; and
- provided that when X is O and --- between C and X is a double bond; then $R_1$ and $R_2$ both are not H.

In one embodiment compounds of formula (I) includes the compounds of structural formula (I'):

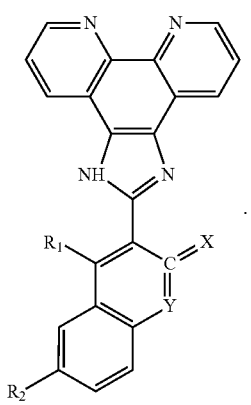

In some embodiments, $R_1$ and $R_2$ are independently H, C1-C6 alkyl, or —O—C1-C6 alkyl. In some embodiments, $R_1$ is H and $R_2$ is H, C1-C6 alkyl, or —O—C1-C6 alkyl. In some embodiments, $R_1$ and $R_2$ are H when X is optionally substituted alkoxy or $NR_3R_4$ and --- between C and X is single bond.

In some embodiments, X is —O—C1-C6 alkyl or $NR_3R_4$. In some embodiments, $R_3$ and $R_4$ are taken together to form a 5 or 6 membered heterocycle, having at least one heteroatom that is N or O.

In one embodiment of the present invention, the compound of Formula I includes the compound of the structural formula (II):

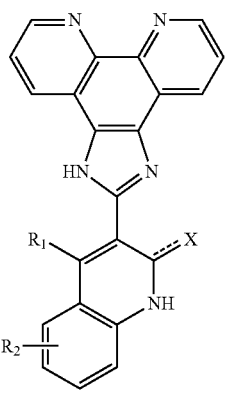

or a salt or solvate thereof, wherein:
- --- designates a single or a double bond;
- X is optionally substituted alkoxy or $NR_3R_4$ when --- is single bond, or
- X is O when --- is a double bond;
- $R_1$ and $R_2$ are independently H, optionally substituted alkyl, or optionally substituted alkoxy; and
- $R_3$ and $R_4$ are taken together to form a 5 or 6 membered optionally substituted heterocycle, having at least one heteroatom that is N or O; and
- provided that when X is O and --- between C and X is a double bond; then $R_1$ and $R_2$ both are not H.

In some embodiments, X is —O—C1-C6 alkyl or $NR_3R_4$, when --- is single bond. In some embodiments, $R_3$ and $R_4$ are taken together to form a 5 or 6 membered heterocycle, having at least one heteroatom that is N or O.

In some embodiments, $R_1$ and $R_2$ are independently H, C1-C6 alkyl, or —O—C1-C6 alkyl. In some embodiments, $R_1$ is H and $R_2$ is H, C1-C6 alkyl, or —O—C1-C6 alkyl.

In another embodiment of the present invention, the compound of Formula I includes the compound of the structural formula (III):

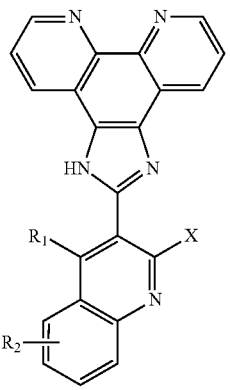

(III)

or a salt or solvate thereof, wherein:
  X is optionally substituted alkoxy or $NR_3R_4$;
  $R_1$ and $R_2$ are independently H, optionally substituted alkyl, or optionally substituted alkoxy; and
  $R_3$ and $R_4$ are taken together to form a 5 or 6 membered optionally substituted heterocycle, having at least one heteroatom that is N or O.

In some embodiments, $R_1$ and $R_2$ are independently H, C1-C6 alkyl, or —O—C1-C6 alkyl. In some embodiments, $R_1$ is H and $R_2$ is H, C1-C6 alkyl, or —O—C1-C6 alkyl.

In some embodiments, X is —O—C1-C6 alkyl. In some embodiments, X is $NR_3R_4$; and $R_3$ and $R_4$ are taken together to form a 5 or 6 membered heterocycle, having at least one heteroatom that is N or O.

In another aspect the present invention, there is provided compounds of formula (IV):

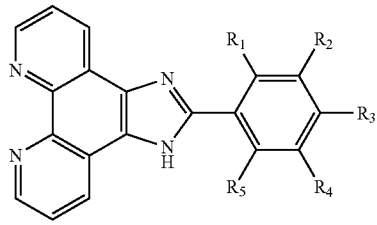

(IV)

or a salt or solvate thereof, wherein:
  one of $R_1$ and $R_2$, or $R_2$ and $R_3$, or $R_3$ and $R_4$, or $R_4$ and $R_5$, when taken together with the carbon atoms, to which they are attached form a 5 or 6 membered optionally substituted heterocycle, having at least one heteroatom that is N or O,
  and remaining of R1 to R5 are independently H, optionally substituted alkyl, or optionally substituted alkoxy.

In some embodiments of the compounds of formula (IV), one of $R_1$ and $R_2$, or $R_2$ and $R_3$, or $R_3$ and $R_4$, or $R_4$ and $R_5$, when taken together with the carbon atoms to which they are attached form:

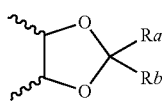

and $R_a$ and $R_b$ are —$R^c$, halo, or —$OR^d$,
  where $R^c$ is selected from the group consisting of alkyl, cycloalkyl, heteroalkyl, cycloheteroalkyl, aryl, arylalkyl, heteroaryl and heteroarylalkyl and $R^d$ is independently hydrogen or $R^c$.

In some embodiments, remaining of R1 to R5 are each H.

In some embodiments, $R_2$ and $R_3$ when taken together with the carbon atoms to which they are attached form:

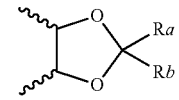

and $R_1$, $R_4$ and $R_5$ are each H.

In some embodiments, $R_a$ and $R_b$ are halo.

The compounds of the present invention include, but are not limited to the following exemplary compounds:

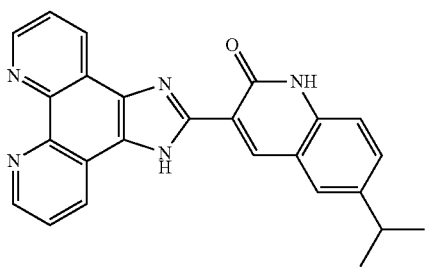

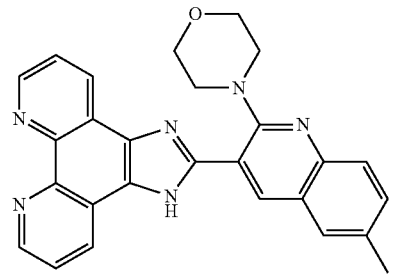

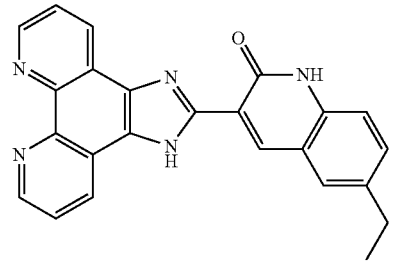

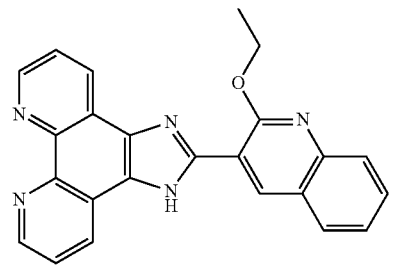

-continued

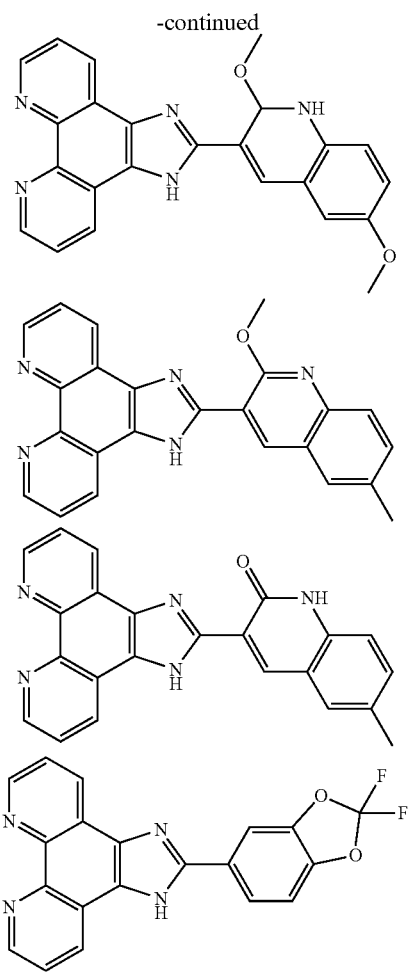

The present invention includes various salts of compounds of the present invention (i.e., the compounds defined by Formula I, Formula IV and their subgenus), including pharmaceutically acceptable salts. Compounds according to the present invention can possess a sufficiently acidic, a sufficiently basic, or both acidic and basic functional groups, and accordingly react with a number of organic and inorganic bases, and organic and inorganic acids, to form pharmaceutically acceptable salts.

The term "pharmaceutically acceptable salt" as used herein, refers to a salt of a compound of Formula I, Formula IV and their subgenus, which is substantially non-toxic to living organisms. Typical pharmaceutically acceptable salts include those salts prepared by reaction of the compound of the present invention with a pharmaceutically acceptable mineral or organic acid or an organic or inorganic base. Such salts are known as acid addition and base addition salts.

Acids commonly employed to form acid addition salts are inorganic acids such as hydrochloric acid, hydrobromic acid, hydroiodic acid, sulphuric acid, phosphoric acid, and the like, and organic acids such as p-toluenesulphonic acid, methanesulphonic acid, oxalic acid, p-bromophenylsulphonic acid, carbonic acid, succinic acid, citric acid, benzoic acid, acetic acid, and the like. Examples of such pharmaceutically acceptable salts are the sulphate, pyrosulphate, bisulphate, sulphite, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulphonate, phenylacetate, phenylpropionate, phenylbutyrate, citrate, lactate, gamma-hydroxybutyrate, glycolate, tartrate, methanesulphonate, propanesulphonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulphonic acid.

Salts of amine groups may also comprise quarternary ammonium salts in which the amino nitrogen carries a suitable organic group such as an alkyl, lower alkenyl, substituted lower alkenyl, lower alkynyl, substituted lower alkynyl, or aralkyl moiety.

Base addition salts include those derived from inorganic bases, such as ammonium or alkali or alkaline earth metal hydroxides, carbonates, bicarbonates, and the like. Bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like.

One skilled in the art will understand that the particular counter ion forming a part of a salt of this invention is usually not of a critical nature, so long as the salt as a whole is pharmacologically acceptable and as long as the counter ion does not contribute undesired qualities to the salt as a whole. The present invention further encompasses the pharmaceutically acceptable solvates of a compound of Formula I, Formula IV or their subgenus. Many of the compounds of the present invention can combine with solvents such as water, methanol, ethanol and acetonitrile to form pharmaceutically acceptable solvates such as the corresponding hydrate, methanolate, ethanolate and acetonitrilate.

The compounds of the present invention may have multiple asymmetric (chiral) centres. As a consequence of these chiral centres, the compounds of the present invention occur as racemates, mixtures of enantiomers and as individual enantiomers, as well as diastereomers and mixtures of diastereomers. All asymmetric forms, individual isomers and combinations thereof, are within the scope of the present invention.

It will be readily understood by one skilled in the art that if the stereochemistry of a compound of Formula I is critical to its activity, then the relative stereochemistry of the compound is established early during synthesis to avoid subsequent stereoisomer separation problems. Further manipulation of the molecule will then employ stereospecific procedures so as to maintain the desired chirality.

II. Preparation of Compounds

As is known in the art, compounds of the present invention can be prepared by a number of standard techniques. Compounds of the present invention, therefore, can be prepared by several general synthetic methods, for example, as described by Grimmett, (Grimmett, M. R., *Comprehensive Heterocyclic Chemistry: The Structure, Reaction, Synthesis and Uses of Heterocyclic Compounds*, A. R. Katrizky and C. W. Rees, eds., Vol. 5, Pergamon Press. Oxford, 1984, pp. 457-498; Grimmett, M. R., *Imidazole and Benzimidazole Synthesis*, Academic Press, San Diego Calif., 1997).

In one embodiment of the present invention, compounds of the present invention are prepared via solution or solid phase synthesis, by reacting a dione of Formula II with the aldehyde (III) in the presence of ammonium acetate in acetic acid (see, for example, Krieg et al., *Naturforsch.* 1967, 22b, 132; Sarshar et al., *Tetrahedron Lett.* 1996, 37, 835-838; Bian et al., *Synthetic communications* 2003, 33, 3477-3482; Hong Xu et al., *J. Chem. Soc., Dalton Trans.,* 2003, 11, 2260-2268; Hong Xu et al., *Inorg. Chem. Commun.,* 2003, 6, 766-768; Bian et al., *Polyhedron* 2002, 21, 313-319; Chao et al., *J. Chem. Soc., Dalton Trans.,* 2001, 12, 1920-1926.

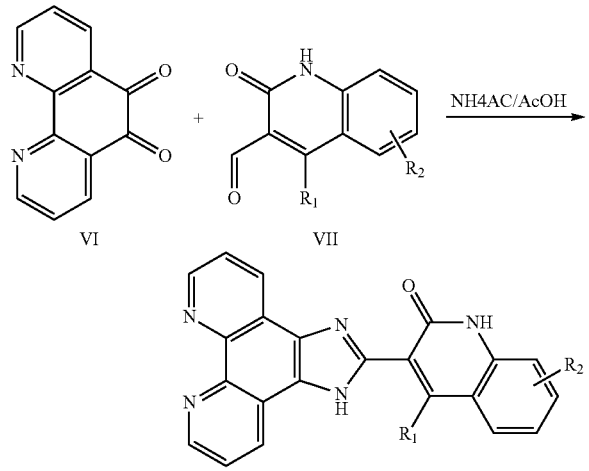

The compounds of Formula (VI) and (VII) are either commercially available or may be prepared using standard procedures known to a person skilled in the relevant art. Compounds of Formula (VI), can be prepared by several general synthetic methods, for example, as described by: Fischer et. al (*J. Am. Chem. Soc.* 1961, 83, 4208-4210); Guijarro et al. (*J. Am. Chem. Soc.* 1999, 121, 4155-4157); Chi et. al. (*Synth. Comm.* 1994, 24(15), 2119-2122) and Armesto et. al. (*Synthesis,* 1988, 799-801); Yamada et. al. (*Bull. Soc Chem. Jpn.,* 1990, 63, (9), 2710-2712); Hiort et. al. (*J. Am. Chem Soc.* 1993, 115, 3448-3454; and Tetrahedron Letters 2004, 45(33), 6361-6363). Compounds of Formula (III) can be prepared by general synthetic methods described by Vilsmeier et. al. (Chem. Ben 1958, 91, 850-861 and Synthesis 1985, 8, 641-645).

The separation and purification of the products (1) is generally based on their property to form water-soluble salts. After the reaction media is diluted with water, the impurities are extracted from the obtained solution with a nonpolar solvent, the aqueous layer is basified and the separated imidazo[4,5-d]phenanthroline (1) is filtered and recrystallized from a suitable solvent.

III. Anti-Cancer Activity of Compounds

The ability of a candidate compound of the present invention to inhibit neoplastic cell growth and/or proliferation can be tested using standard techniques known in the art. In addition, compounds of the present invention that demonstrate inhibitory activity may be further tested in vitro and/or in vivo in combination with various known chemotherapeutics to evaluate their potential use in combination therapies. Exemplary methods of testing candidate compounds of the present invention are provided below and in the Examples included herein. One skilled in the art will understand that other methods of testing the compounds are known in the art and are also suitable for testing candidate compounds.

A. In Vitro Testing

Candidate compounds of the present invention are assayed initially in vitro for their ability to inhibit proliferation of cancer cells using standard techniques.

In general, the ability of a candidate compound of Formula 1 to inhibit proliferation of cancer cells can be tested as follows. Cells of a specific test cancer cell line are grown to a suitable density (e.g. approximately $1\times10^4$) and various concentrations of the candidate compound are added. After an appropriate incubation time (typically between about 48 to 74 hours), cell survival is assessed, for example, by assaying for tetrazolium salt (or modified tetrazolium salt) cleavage, or by using the resazurin reduction test (see Fields & Lancaster (1993) *Am. Biotechnol. Lab.* 11:48-50; O'Brien et al., (2000) *Eur J. Biochem.* 267:5421-5426 and U.S. Pat. No. 5,501, 959), the sulforhodamine assay (Rubinstein et al., (1990) *J. Natl. Cancer Inst.* 82:113-118), the neutral red dye test (Kitano et al., (1991) *Euro. J. Clin. Investg.* 21:53-58; West et al., (1992) *J. Investigative Dean.* 99:95-100) or the XTT assay. Inhibition of cell proliferation is determined by comparison of cell survival in the treated culture with cell survival in one or more control cultures, for example, cultures not pre-treated with the candidate compound, those pre-treated with a control vehicle and/or those pre-treated with a control compound (typically a known therapeutic).

Other assays known in the art that measure metabolic activity (such as tetrazolium-based assays) can also be used to assess the effect of candidate compounds on cell proliferation, given that proliferating cells tend to be metabolically more active than resting cells.

Candidate compounds can also be tested in vitro for their ability to inhibit anchorage-independent growth of tumour cells. Anchorage-independent growth is known in the art to be a good indicator of tumorigenicity. In general, anchorage-independent growth is assessed by plating cells from an appropriate cancer cell-line onto soft agar and determining the number of colonies formed after an appropriate incubation period. Growth of cells treated with the candidate compound can then be compared with that of cells treated with an appropriate control (as described above).

A wide variety of cancer cell lines suitable for testing the compounds of the present invention are available commercially, for example the American Type Culture Collection (ATCC; Manassas, Va.) currently supplies over 700 different human cancer cell lines and the DCTD Tumor Depository (NCI at Frederick, Frederick, Md.) supplies a variety of mammalian cell lines, including the human cancer cell lines used in the NCI/NIH screen.

Examples of suitable human cancer cell-lines against which the compounds of the present invention can be tested include, but are not limited to, bladder cancer cell lines HT-1376, HT-1197, and Hs 195.T; colon and colorectal adenocarcinoma and carcinoma cell lines such as CaCo, COL0320, HCT-116, LoVo, NCI-H498, NCI-H548 and SNU-C2B; duodenal cancer cell line HuTu 80; gastric adenocarcinoma and carcinoma cell lines Hs 740.T, AGS, Hs 746T, NCI-N87, NCI-SNU-1 and RF-48; large cell lung cancer cell lines NCI-H661 and NCI-H1581; prostate adenocarcinoma and carcinoma cell lines MDA PCa 2b, LNCaP-FGC and 22Rv1; Burkitts lymphoma (Non-Hodgkin's) cell lines raji, Namalwa and HS Sultan; histiocytic lymphoma cell line U-937; acute lymphoblastic leukemia (T-ALL) cell line Jurkat, T-cell lymphoma cell line Karpas 299; plasma cell leukemia cell line L-363; and rectal adenocarcinoma and carcinoma cell lines NCI-H630 and SW837. Drug-resistant cancer cell lines can also be used to determine the ability of the compounds of the present invention to inhibit growth and/or proliferation of drug- or multi-drug resistant neoplastic cells.

The differential neoplastic selectivity of the candidate compounds of the present invention can also be tested, i.e. the ability of the compound to demonstrate some level of selective action toward neoplastic (or cancer) cells in comparison to normal proliferating cells. An exemplary method of assessing the differential sensitivity between normal and cancer cells for a compound has been described by Vassilev et al. (*Anti-Cancer Drug Design* (2001) 16:7). This method involves the comparison of $IC_{90}$ values, i.e. the molar concentration of a test compound required to cause 90% growth inhibition of exponentially growing cells. Thus, the $IC_{90}$ values for candidate compounds can be evaluated in various cancer cell lines (such as those outlined above) and normal cells (such as HUVEC and/or WI38 cells) and compared. $IC_{90}$ values can be measured using a variety of standard techniques as known in the art. Cancer cell selectivity is calculated as a ratio between the average $1C_{90}$ for all normal cell lines and the average $1C_{90}$ for all cancer cell lines. Compounds with an $1C_{90}$ ratio (normal/cancer) of >4 are considered to be selective for cancer cells (L. T. Vassilev et al., Anti-cancer Drug Design, 2001, 16: 7-17).

While the mechanism of action of the compounds of the present invention is not relevant to the instant invention, assays to investigate potential mechanisms of action of the compounds may be conducted if desired in order to provide information useful in determining what aspects of tumour growth the compounds affect. This type of information may help to determine cancer types that will benefit from treatment with the compounds. Examples of such assays include, but are not limited to, cell-cycle analysis (for example, employing flow cytometry techniques), apoptosis assays (such as DNA fragmentation analysis), anti-angiogenesis assays (for example, various Matrigel assays, including cord formation and Matrigel plug assays) and immunohistochemical analysis.

TABLE 1

Cancer cell lines used in the NCI/NIH Developmental Therapeutics Program in vitro Screen

| Cancer Type | Cell Line | |
|---|---|---|
| Breast | MCF7 | MDA-MB-435 |
| | NCI/ADR-RES | MDA-N |
| | MDA-MB-231/ATCC | BT-549 |
| | HS 578T | T-47D |
| CNS | SF-268 | SNB-19 |
| | SF-295 | SNB-75 |
| | SF-539 | U251 |
| Colon | COLO 205 | HT29 |
| | HCC-2998 | KM12 |
| | HCT-116 | SW-620 |
| | HCT-15 | |
| Leukemia | CCRF-CEM | MOLT-4 |
| | HL-60(TB) | RPMI-8226 |
| | K-562 SR | |
| Melanoma | LOX IMVI | SK-MEL-28 |
| | MALME-3M | SK-MEL-5 |
| | M14 | UACC-257 |
| | SK-MEL-2 | UACC-62 |
| Non-Small Cell Lung | A549/ATCC | NCI-H23 |
| | EKVX | NCI-H322M |
| | HOP-62 | NCI-H460 |
| | HOP-92 | NCI-H522 |
| | NCI-H226 | |
| Ovarian | IGR-OV1 | OVCAR-5 |
| | OVCAR-3 | OVCAR-8 |
| | OVCAR-4 | SK-OV-3 |

TABLE 1-continued

Cancer cell lines used in the NCI/NIH Developmental Therapeutics Program in vitro Screen

| Cancer Type | Cell Line | |
|---|---|---|
| Prostate | PC-3 | |
| | DU-145 | |
| Renal | 786-0 | RXF 393 |
| | A498 | SN12C |
| | ACHN | TK-10 |
| | CAKI-1 | UO-31 |

B. In Vivo Testing

The ability of the candidate compounds to inhibit tumour growth, proliferation and/or metastasis in vivo can be determined in an appropriate animal model using standard techniques known in the art (see, for example, Enna, et al., *Current Protocols in Pharmacology*, J. Wiley & Sons, Inc., New York, N.Y.). Exemplary protocols are provided below and in the Examples.

For example, the in vivo activity of candidate compounds can also be tested using the Hollow Fiber Assay (Hollingshead, M., et al., (1995) *Life Sciences* 57:131-141; and Decker et al., *Eur. J. of Cancer* 40: 821-826 (2004)). In this assay, cells growing in hollow fibers (polyvinylidine fluoride, PVDF) are implanted in various body compartments of mice. A standard panel of 12 tumour cell lines can be used for the hollow fiber screening of candidate compounds which have shown activity in vitro. These cell lines may include NCI-H23, NCI-H522, MDA-MB-231, MDA-MB-435, SW-620, COLO 205, LOX-IMVI, UACC-62, OVCAR-3, OVCAR-5, U251 and SF-295. In addition, alternate lines such as those described in the above in vitro section can be used for specialized testing of compounds. The cell lines are cultivated according to standard protocols, and fibers are prepared by flushing cells into the PVDF fibers and sealing them at 2 cm intervals. The samples generated from these seals are placed into tissue culture medium and incubated at 37° C. in 5% $CO_2$ for 24 to 48 hours prior to implantation. A total of 3 different tumour lines are prepared for each experiment so that each mouse receives 3 intraperitoneal implants (1 of each tumour line) and 3 subcutaneous implants (1 of each tumour line). On the day of implantation, samples of each tumour cell line preparation are quantitated for viable cell mass by, for example, a stable endpoint MTT assay, so that the time zero cell mass is known. Mice are treated with experimental agents starting on day 3 or 4 following fiber implantation and continuing daily for 4 days. Each agent is administered by intraperitoneal injection at 2 dose levels. The fibers are collected from the mice on the day following the fourth compound treatment and subjected to the stable endpoint MTT assay. The optical density of each sample is determined spectrophotometrically at 540 nm and the mean of each treatment group is calculated. The percent net growth for each cell line in each treatment group is calculated and compared to the percent net growth in the vehicle treated controls. A 50% or greater reduction in percent net growth in the treated samples compared to the vehicle control samples is considered a positive result. Each positive result is given a score of 2 and all of the scores are totaled for a given compound. The maximum possible score for an agent is 96 (12 cell lines×2 sites×2 dose levels×2 [score]).

A candidate compound that is screened initially in the hollow fiber assay may subsequently be tested in a xenograft model if it has a combined ip+sc score of 20 or greater, a sc score of 8 or greater, or produces cell kill of any cell line at either dose level evaluated. This scoring system has been validated by DCTDC statisticians in CTEP to represent a level of detection expected to score current "standard" agents as active.

Alternatively, compounds of the present invention can be tested directly in xenograft models. Xenograft models, in which a human tumour has been implanted into an animal, are a standard model in which to assess the anti-cancer activity of a candidate compound. Examples of xenograft models of human cancer include, but are not limited to, human solid tumour xenografts, implanted by sub-cutaneous injection or implantation and used in tumour growth assays; human solid tumour isografts, implanted by fat pad injection and used in tumour growth assays; human solid tumour orthotopic xenografts, implanted directly into the relevant tissue and used in tumour growth assays; disseminated disease models for solid tumours or for leukemias, via intravenous injection, used in survival assays; experimental models of lymphoma and leukaemia in mice, used in survival assays, and experimental models of lung metastasis in mice. In addition to the implanted human tumour cells, the xenograft models can further comprise transplanted human peripheral blood leukocytes, which allow for evaluation of the anti-cancer immune response. In various xenograft models, the implanted or transplanted human tumour cells can be primary tumour cells or tumour cells derived from a cell line.

Several host animal options exist for xenograft models, which includes but is not limited to the use of severe combined immunodeficient (SCID) mice, athymic nude mice, and athymic rats. Non-obese diabetic/severe combined immunodeficient mice (NOD/SCID) represent another host animal that can be used in various xenograft transplantation models, for example, for the engraftment of hematological cancer cells, such as leukemia and/or lymphoma cells.

Alternatively, murine cancer models can be used for screening anti-tumour compounds. Examples of appropriate murine cancer models are known in the art and include, but are not limited to, implantation models in which murine cancer cells are implanted by intravenous, subcutaneous, fat pad or orthotopic injection; murine metastasis models; transgenic mouse models; and knockout mouse models. The effect of the candidate compound can also be assessed on spontaneous tumours in normal mice.

For example, the candidate compounds can be tested in vivo on solid tumours using mice that are subcutaneously grafted or injected with 30 to 60 mg of a tumour fragment, or an appropriate number of tumour cells (e.g. about $10^6$ to $10^7$) on day 0. The animals bearing tumours are mixed before being subjected to the various treatments and controls. In the case of treatment of advanced tumours, tumours are allowed to develop to the desired size, animals having insufficiently developed tumours being eliminated. The selected animals are distributed at random to undergo the treatments and controls. Animals not bearing tumours may also be subjected to the same treatments as the tumour-bearing animals in order to be able to dissociate the toxic effect from the specific effect on the tumour. Chemotherapy generally begins from 3 to 22 days after grafting, depending on the type of tumour, and the animals are observed every day. Candidate compounds can be administered to the animals, for example, by bolus infusion. The different animal groups are weighed about 3 or 4 times a week until the maximum weight loss is attained, after which the groups are weighed at least once a week until the end of the trial.

The tumours are measured about 2 or 3 times a week until the tumour reaches a pre-determined size and/or weight, or until a pre-determined time period has passed, or until the animal dies (if this occurs before the tumour reaches the pre-determined size/weight). The animals are then sacrificed and the tissue histology, size and/or proliferation of the tumour assessed.

The effect of the candidate compounds on drug-resistant tumours can be assessed in vivo by utilising a drug- or multidrug-resistant cancer cell in the xenograft experiments.

For the study of the effect of the candidate compounds on haematologic tumours, such as lymphomas or leukaemias, the animals are grafted or injected with a particular number of cells, and the anti-tumour activity is determined by the increase in the survival time of the treated mice relative to the controls. Assessing disease burden in leukemia xenograft models can also be performed by measuring various indicators of leukemia, such as cell surface markers or expression of leukemia specific genes, using flow cytometry or polymerase chain reaction (PCR) from serial blood samples.

To study the effect of the candidate compounds on tumour metastasis, tumour cells are typically treated with the compound ex vivo and then injected into a suitable test animal. The spread of the tumour cells from the site of injection is then monitored over a suitable period of time.

The ability of the candidate compounds to act in combination with, or to sensitise a tumour to the effects of, another chemotherapeutic agent can also be tested in the above models. In this case, the test animals would be treated with both the chemotherapeutic agent and the candidate compound of Formula I. Control animals could include animals treated with the chemotherapeutic alone, animals treated with the candidate compound alone and/or untreated animals.

In vivo toxic effects of the compounds of the present invention can be evaluated by standard techniques, for example, by measuring their effect on animal body weight during treatment and by performing haematological profiles and liver enzyme analysis after the animal has been sacrificed (survival assays).

TABLE 2

Examples of in vivo models of human cancer

| Cancer Model | Cell Type |
|---|---|
| Tumour Growth Assay Human solid tumour xenografts in mice (sub-cutaneous injection) | Prostate (PC-3, DU145) Breast (MDA-MB-231, MVB-9) Colon (HT-29) Lung (NCI-H460, NCI-H209) Pancreatic (ASPC-1, SU86.86) Pancreatic: drug resistant (BxPC-3) Skin (A2058, C8161) Cervical (SIHA, HeLa-S3) Cervical: drug resistant (HeLa S3-HU-resistance) Liver (HepG2) Brain (U87-MG) Renal (Caki-1, A498) Ovary (SK-OV-3) Bladder (T24) |
| Tumour Growth Assay Human solid tumour isografts in mice (fat pad injection) | Breast: drug resistant (MDA-CDDP-S4, MDA-MB435-To.1) |
| Survival Assay Experimental model of lymphoma and leukaemia in mice | Human: Burkitts lymphoma (Non-Hodgkin's) (raji, Namalwa, HS Sultan), histiocytic lymphoma (U-937), chronic myelogenous leukemia (K-562), acute lymphoblastic leukemia (T-ALL) (Jurkat, CEM, MOLT-4), T-cell lymphoma (Karpas 299), plasma cell leukemia (L-363) Murine: erythroleukemia (CB7 Friend retrovirus-induced), lymphocytic leukemia (L1210), lymphoma (P388) |

TABLE 2-continued

Examples of in vivo models of human cancer

| Cancer Model | Cell Type |
| --- | --- |
| Experimental model of lung metastasis in mice | Human: melanoma (C8161) Murine: fibrosarcoma (R3) |

Methods of carrying out these assays are known in the art as described above.

C. Toxicity Testing The compounds of the present invention can also be submitted to toxicity testing if desired.

Toxicity tests for potential drugs are well-known in the art (see, for example, Hayes, A. W., ed., (1994), *Principles and Methods of Toxicology*, 3$^{rd}$ ed., Raven Press, NY; Maines, M., ed., *Current Protocols in Toxicology*, John Wiley & Sons, Inc., NY).

Toxicity of the candidate compounds can also be initially assessed in vitro using standard techniques. For example, human primary fibroblasts can be treated in vitro with a compound of Formula I and then tested at different time points following treatment for their viability using a standard viability assay, such as the assays described above or the trypan-blue exclusion assay. Cells can also be assayed for their ability to synthesize DNA, for example, using a thymidine incorporation assay, and for changes in cell cycle dynamics, for example, using a standard cell sorting assay in conjunction with a fluorocytometer cell sorter (FACS).

In vitro acute toxicity testing of a compound of Formula I can be performed using mammalian cell lines (see, for example, Ekwall, B., *Ann. N.Y. Acad. Sci.*, (1983) 407:64-77). Selection of an appropriate cell line is dependent on the potential application of the candidate compound and can be readily determined by one skilled in the art. For example, these tests include the treatment of human primary fibroblasts in vitro with the compounds of the present invention in the presence of a commercial carrier. Cells are then tested at different time points following treatment for their viability using a standard viability assay, such as the trypan-blue exclusion assay, XTT or MTT assays. Cells can also be assayed for their ability to synthesize DNA, for example, using a thymidine incorporation assay, and for changes in cell cycle dynamics, for example, using a standard cell sorting assay in conjunction with a fluorocytometer cell sorter (FACS).

In vivo toxicity testing can be performed by standard methodology, for example, by injecting varying concentrations of the candidate compound into an appropriate animal model. The compound can be injected once, or administration can be repeated over several days. The toxic effects of the compound can be evaluated over an appropriate time period by monitoring the mortality, changes in behavior, appearance, and body weight of the animals. After the completion of the period of assessment, the animals can be sacrificed and the appearance and weight of the relevant organs determined. If necessary, additional assessments of, for example, hematological profiles, histology, and liver enzyme analysis may be performed. An indication of the toxicity of a compound can also be obtained during the in vivo anti-cancer testing of the compound.

IV. Uses of Compounds

Compounds of the present invention can be used to treat, stabilize or prevent cancer in a subject. In this context, the compounds may exert either a cytotoxic or cytostatic effect resulting in a reduction in the size of a tumour, the slowing or prevention of an increase in the size of a tumour, an increase in the disease-free survival time between the disappearance or removal of a tumour and its reappearance, prevention of an initial or subsequent occurrence of a tumour (e.g. metastasis), an increase in the time to progression, reduction of one or more adverse symptom associated with a tumour, or an increase in the overall survival time of a subject having cancer.

Exemplary tumours include, but are not limited to, haematologic neoplasms, including leukaemias, myelomas and lymphomas; carcinomas, including adenocarcinomas and squamous cell carcinomas; melanomas and sarcomas. Carcinomas and sarcomas are also frequently referred to as "solid tumours." Examples of commonly occurring solid tumours include, but are not limited to, cancer of the brain, breast, cervix, colon, head and neck, kidney, lung, ovary, pancreas, prostate, stomach and uterus, non-small cell lung cancer and colorectal cancer. Various forms of lymphoma also may result in the formation of a solid tumour and, therefore, are also often considered to be solid tumours.

The cancers which can be treated in accordance with one embodiment of the present invention thus include, but are not limited to, leukaemias; adenocarcinomas and carcinomas, including squamous cell carcinomas. Carcinomas are also frequently referred to as "solid tumours," as described above, and examples of commonly occurring solid tumours that can be treated in accordance with the present invention include, but are not limited to, anal cancer, bladder cancer, colon cancer, colorectal cancer, duodenal cancer, gastric (stomach) cancer, lung (non-small cell) cancer, oesophageal cancer, prostate cancer, rectal cancer and small intestine cancer. Accordingly, one embodiment of the present invention provides for the use of a compound of Formula I in the treatment of a cancer selected from the group of leukemia, bladder cancer, lung (non-small cell) cancer, prostate cancer and a cancer of the GI tract, wherein cancers of the GI tract include, but are not limited to, anal cancer, colon cancer, colorectal cancer, duodenal cancer, gastric (stomach) cancer, oesophageal cancer, rectal cancer and small intestine cancer.

One embodiment of the present invention provides for the use of the compounds of the present invention in the treatment of one or more of prostate cancer, non-small cell lung cancer, colon cancer, renal cancer, pancreatic cancer, leukemia, lymphoma and/or brain cancer/tumour.

The term "leukaemia" refers broadly to progressive, malignant diseases of the blood-forming organs. Leukaemia is typically characterized by a distorted proliferation and development of leukocytes and their precursors in the blood and bone marrow but can also refer to malignant diseases of other blood cells such as erythroleukaemia, which affects immature red blood cells. Leukaemia is generally clinically classified on the basis of (1) the duration and character of the disease—acute or chronic; (2) the type of cell involved—myeloid (myelogenous), lymphoid (lymphogenous) or monocytic, and (3) the increase or non-increase in the number of abnormal cells in the blood—leukaemic or aleukaemic (subleukaemic). Leukaemia includes, for example, acute nonlymphocytic leukaemia, chronic lymphocytic leukaemia, acute granulocytic leukaemia, chronic granulocytic leukaemia, acute promyelocytic leukaemia, adult T-cell leukaemia, aleukaemic leukaemia, aleukocythemic leukaemia, basophylic leukaemia, blast cell leukaemia, bovine leukaemia, chronic myelocytic leukaemia, leukaemia cutis, embryonal leukaemia, eosinophilic leukaemia, Gross' leukaemia, hairy-cell leukaemia, hemoblastic leukaemia, hemocytoblastic leukaemia, histiocytic leukaemia, stem cell leukaemia, acute monocytic leukaemia, leukopenic leukaemia, lymphatic leukaemia, lymphoblastic leukaemia, lymphocytic leukaemia, lymphogenous leukaemia, lymphoid leukaemia, lymphosarcoma cell leukaemia, mast cell leukaemia, megakaryocytic leukaemia, micromyeloblastic leukaemia, monocytic leukaemia, myeloblastic leukaemia, myelocytic leukaemia, myeloid granulocytic leukaemia, myelomonocytic leukaemia, Naegeli leukaemia, plasma cell leukaemia, plasmacytic leukaemia, promyelocytic leukaemia, Rieder cell leukaemia, Schilling's leukaemia, stem cell leukaemia, subleukaemic leukaemia, and undifferentiated cell leukaemia.

The term "carcinoma" refers to a malignant new growth made up of epithelial cells tending to infiltrate the surrounding tissues and give rise to metastases. The term "carcinoma" also encompasses adenocarcinomas. Adenocarcinomas are carcinomas that originate in cells that make organs which have glandular (secretory) properties or that originate in cells that line hollow viscera, such as the gastrointestinal tract or bronchial epithelia, and include adenocarcinomas of the lung and prostate.

In accordance with the present invention, the compounds according to Formula I, Formula IV and their subgenus can be used to treat various stages and grades of cancer cell, tumour and/or cancer development and progression. The present invention, therefore, contemplates the use of the combinations in the treatment of early stage cancers including early neoplasias that may be small, slow growing, localized and/or nonaggressive, for example, with the intent of curing the disease or causing regression of the cancer, as well as in the treatment of intermediate stage and in the treatment of late stage cancers including advanced and/or metastatic and/or aggressive neoplasias, for example, to slow the progression of the disease, to reduce metastasis or to increase the survival of the patient. Similarly, the combinations may be used in the treatment of low grade cancers, intermediate grade cancers and or high grade cancers.

The present invention also contemplates that the compounds can be used in the treatment of indolent cancers, recurrent cancers including locally recurrent, distantly recurrent and/or refractory cancers (i.e. cancers that have not responded to treatment), metastatic cancers, locally advanced cancers and aggressive cancers. Thus, an "advanced" cancer includes locally advanced cancer and metastatic cancer and refers to overt disease in a patient, wherein such overt disease is not amenable to cure by local modalities of treatment, such as surgery or radiotherapy. The term "metastatic cancer" refers to cancer that has spread from one part of the body to another. Advanced cancers may also be unresectable, that is, they have spread to surrounding tissue and cannot be surgically removed.

One skilled in the art will appreciate that many of these categories may overlap, for example, aggressive cancers are typically also metastatic. "Aggressive cancer," as used herein, refers to a rapidly growing cancer. One skilled in the art will appreciate that for some cancers, such as breast cancer or prostate cancer the term "aggressive cancer" will refer to an advanced cancer that has relapsed within approximately the earlier two-thirds of the spectrum of relapse times for a given cancer, whereas for other types of cancer, such as small cell lung carcinoma (SCLC) nearly all cases present rapidly growing cancers which are considered to be aggressive. The term can thus cover a subsection of a certain cancer type or it may encompass all of other cancer types.

The compounds may also be used to treat drug resistant cancers, including multidrug resistant tumours. As is known in the art, the resistance of cancer cells to chemotherapy is one of the central problems in the management of cancer.

Certain cancers, such as prostate, can be treated by hormone therapy, i.e. with hormones or anti-hormone drugs that slow or stop the growth of certain cancers by blocking the body's natural hormones. Such cancers may develop resistance, or be intrinsically resistant, to hormone therapy. The present invention further contemplates the use of the compounds in the treatment of such "hormone-resistant" or "hormone-refractory" cancers.

The present invention also contemplates the use of the compounds as "sensitizing agents," which selectively inhibit the growth of cancer cells. In this case, the compound alone does not have a cytotoxic effect on the cancer cell, but provides a means of weakening the cancer cells, and better facilitate the benefit obtained from the application of conventional anti-cancer therapeutics, or to otherwise potentiate said therapeutics.

Thus, the present invention contemplates the administration to a subject of a therapeutically effective amount of one or more compounds together with one or more anti-cancer therapeutics. The compound(s) can be administered before, during or after treatment with the anti-cancer therapeutic. An "anti-cancer therapeutic" is a compound, composition or treatment that prevents or delays the growth and/or metastasis of cancer cells. Such anti-cancer therapeutics include, but are not limited to, chemotherapeutic drug treatment, radiation, gene therapy, hormonal manipulation, immunotherapy and antisense oligonucleotide therapy. Examples of useful chemotherapeutic drugs include, but are not limited to, hydroxyurca, busulphan, cisplatin, carboplatin, chlorambucil, melphalan, cyclophosphamide, Ifosphamide, danorubicin, doxorubicin, epirubicin, mitoxantrone, vincristine, vinblastine, Navelbine® (vinorelbine), etoposide, teniposide, paclitaxel, docetaxel, gemcitabine, cytosine, arabinoside, bleomycin, neocareinostatin, suramin, taxol, mitomycin C and the like. The compounds of the invention are also suitable for use with standard combination therapies employing two or more chemotherapeutic agents. It is to be understood that anti-cancer therapeutics for use in the present invention also include novel compounds or treatments developed in the future.

V. Pharmaceutical Compositions

The compounds of the present invention are typically formulated prior to administration. The present invention thus provides pharmaceutical compositions comprising one or more compounds of the present invention and a pharmaceutically acceptable carrier, diluent, or excipient. The pharmaceutical compositions are prepared by known procedures using well-known and readily available ingredients. Pharmaceutical compositions comprising one or more compounds of the present invention in combination with one or more known cancer chemotherapeutics are also contemplated by the present invention.

Compounds of the present invention or pharmaceutical compositions comprising the compounds may be administered orally, topically, parenterally, by inhalation or spray, or rectally in dosage unit formulations containing conventional non-toxic pharmaceutically acceptable carriers, adjuvants and vehicles. In the usual course of therapy, the active compound is incorporated into an acceptable vehicle to form a composition for topical administration to the affected area, such as hydrophobic or hydrophilic creams or lotions, or into a form suitable for oral, rectal or parenteral administration, such as syrups, elixirs, tablets, troches, lozenges, hard or soft capsules, pills, suppositories, oily or aqueous suspensions, dispersible powders or granules, emulsions, injectables, or solutions. The term parenteral as used herein includes subcutaneous injections, intradermal, intra-articular, intravenous, intramuscular, intravascular, intrasternal, intrathecal injection or infusion techniques.

The present invention also provides for pharmaceutical compositions comprising one or more of the compounds of the present invention and a vehicle, such as an artificial membrane vesicle (including a liposome, lipid micelle and the like), microparticle or microcapsule.

Compositions intended for oral use may be prepared in either solid or fluid unit dosage forms. Fluid unit dosage form can be prepared according to procedures known in the art for the manufacture of pharmaceutical compositions and such compositions may contain one or more agents selected from the group consisting of sweetening agents, flavouring agents, colouring agents and preserving agents in order to provide pharmaceutically elegant and palatable preparations. An elixir is prepared by using a hydroalcoholic (e.g., ethanol) vehicle with suitable sweeteners such as sugar and saccharin, together with an aromatic flavoring agent. Suspensions can be prepared with an aqueous vehicle with the aid of a suspending agent such as acacia, tragacanth, methylcellulose and the like.

Solid formulations such as tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate: granulating and disintegrating agents for example, corn starch, or alginic acid: binding agents, for example starch, gelatin or acacia, and lubricating agents, for example magnesium stearate, stearic acid or talc and other conventional ingredients such as dicalcium phosphate, magnesium aluminum silicate, calcium sulfate, starch, lactose, methylcellulose, and functionally similar materials. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil. Soft gelatin capsules are prepared by machine encapsulation of a slurry of the compound with an acceptable vegetable oil, light liquid petrolatum or other inert oil.

Aqueous suspensions contain active materials in admixture with excipients suitable for the manufacture of aqueous suspensions. Such excipients are suspending agents, for example sodium carboxylmethylcellulose, methyl cellulose, hydropropylmethylcellulose, sodium alginate, polyvinylpyrrolidone, gum tragacanth and gum acacia: dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example hepta-decaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl-p-hydroxy benzoate, one or more colouring agents, one or more flavouring agents or one or more sweetening agents, such as sucrose or saccharin.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

Pharmaceutical compositions of the invention may also be in the form of oil-in-water emulsions. The oil phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

The pharmaceutical compositions may be in the form of a sterile injectable aqueous or oleaginous suspension. This suspension may be formulated according to known art using those suitable dispersing or wetting agents and suspending agents that have been mentioned above. The sterile injectable preparation may also be a sterile injectable solution or a suspension in a non-toxic parentally acceptable diluent or solvent, for example as a solution in 1,3-butanediol.

Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables. Adjuvants such as local anesthetics, preservatives and buffering agents can also be included in the injectable solution or suspension.

The compound(s) of the general Formula I may be administered, together or separately, in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols.

Other pharmaceutical compositions and methods of preparing pharmaceutical compositions are known in the art and are described, for example, in "*Remington: The Science and Practice of Pharmacy*" (formerly "*Remingtons Pharmaceutical Sciences*"); Gennaro, A., Lippincott, Williams & Wilkins, Philadelphia, Pa. (2000).

VI. Administration of Compounds

Compounds of the present invention may be administered to a subject by a variety of routes depending on the cancer to be treated, for example, the compounds may be administered orally, topically, parenterally, by inhalation or spray, or rectally in dosage unit formulations. In one embodiment, the compounds are administered systemically to a subject, for example, by bolus injection or infusion into a subject's bloodstream or by oral administration. When used in conjunction with one or more known chemotherapeutic agents, the compounds can be administered prior to, or after, administration of the chemotherapeutic agents, or they can be administered concomitantly. The one or more chemotherapeutic may also be administered systemically, for example, by bolus injection, infusion, or oral administration.

The compounds of the present invention may be used as part of a neo-adjuvant therapy (to primary therapy), or as part of an adjuvant therapy regimen. The present invention contemplates the use of the compounds of the present invention at various stages in tumour development and progression, including in the treatment of advanced and/or aggressive neoplasias (i.e. overt disease in a subject that is not amenable to cure by local modalities of treatment, such as surgery or radiotherapy), metastatic disease, locally advanced disease and/or refractory tumours (i.e. a cancer or tumour that has not responded to treatment).

"Primary therapy" refers to a first line of treatment upon the initial diagnosis of cancer in a subject. Exemplary primary therapies may involve surgery, a wide range of chemotherapies and radiotherapy. "Adjuvant therapy" refers to a therapy that follows a primary therapy and that is administered to subjects at risk of relapsing. Adjuvant systemic therapy is usually begun soon after primary therapy to delay recurrence, prolong survival or cure a subject.

It is contemplated that the compounds of the invention can be used alone or in combination with one or more other chemotherapeutic agents as part of a primary therapy or an adjuvant therapy. Combinations of the compounds of the present invention and standard chemotherapeutics may act to improve the efficacy of the chemotherapeutic and, therefore, can be used to improve standard cancer therapies. This application can be important in the treatment of drug-resistant cancers which are not responsive to standard treatment. Drug-resistant cancers can arise, for example, from heterogeneity of tumour cell populations, alterations in response to chemotherapy and increased malignant potential. Such changes are often more pronounced at advanced stages of disease.

The dosage to be administered is not subject to defined limits, but it will usually be an effective amount. It will usually be the equivalent, on a molar basis of the pharmacologically active free form produced from a dosage formulation upon the metabolic release of the active free drug to achieve its desired pharmacological and physiological effects. The compositions may be formulated in a unit dosage form. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient. Examples of ranges for the compound(s) in each dosage unit are from about 0.05 to about 100 mg, or more usually, from about 1.0 to about 50 mg.

Daily dosages of the compounds of the present invention will typically fall within the range of about 0.01 to about 100 mg/kg of body weight, in single or divided dose. However, it will be understood that the actual amount of the compound(s) to be administered will be determined by a physician, in the light of the relevant circumstances, including the condition to be treated, the chosen route of administration, the actual compound administered, the age, weight, and response of the individual patient, and the severity of the patient's symptoms. The above dosage range is given by way of example only and is not intended to limit the scope of the invention in any way. In some instances dosage levels below the lower limit of the aforesaid range may be more than adequate, while in other cases still larger doses may be employed without causing harmful side effects, for example, by first dividing the larger dose into several smaller doses for administration throughout the day.

VII. Clinical Trials in Cancer Patients

One skilled in the art will appreciate that, following the demonstrated effectiveness of a compound of Formula I in vitro and in animal models, it can be submitted to standard GLP animal toxicology and pharmacokinetic studies and then be entered into Clinical Trials in order to further evaluate its efficacy in the treatment of cancer and to obtain regulatory approval for therapeutic use. As is known in the art, clinical trials progress through phases of testing, which are identified as Phases I, II, III, and IV.

Initially, the selected compound of Formula I will be evaluated in a Phase I trial, which is usually an open-label trial. Typically Phase I trials are used to determine the best mode of administration (for example, by pill or by injection), the frequency of administration, and the toxicity for the compound. Phase I studies frequently include laboratory tests, such as blood tests and biopsies, to evaluate the effects of the compound of Formula I in the body of the patient. For a Phase I trial, a small group of cancer patients are treated with a specific dose of the compound of Formula I. During the trial, the dose is typically increased group by group in order to determine the maximum tolerated dose (MTD) and the dose-limiting toxicities (DLT) associated with the compound. This process determines an appropriate dose to use in a subsequent Phase II trial. A Phase II trial can be conducted to further evaluate the effectiveness and safety of the compounds according to the present invention. In Phase II trials, these compounds are administered to groups of patients with either one specific type of cancer or with related cancers, using the dosage found to be effective in Phase I trials.

Phase III trials focus on determining how a compound compares to the standard, or most widely accepted, treatment. In Phase III trials, patients are randomly assigned to one of two or more "arms". In a trial with two arms, for example, one arm will receive the standard treatment (control group) and the other arm will receive treatment with a compound according to the present invention (investigational group).

Phase IV trials are used to further evaluate the long-term safety and effectiveness of a compound. Phase IV trials are less common than Phase I, II and III trials and will take place after the compound has been approved for standard use.

A. Eligibility of Patients for Clinical Trials

Participant eligibility criteria can range from general (for example, age, sex, type of cancer) to specific (for example, type and number of prior treatments, tumour characteristics, blood cell counts, organ function). Eligibility criteria may also vary with trial phase. For example, in Phase I and II trials, the criteria often exclude patients who may be at risk from the investigational treatment because of abnormal organ function or other factors. In Phase II and III trials additional criteria are often included regarding disease type and stage, and number and type of prior treatments.

Phase I cancer trials usually comprise 15 to 30 participants for whom other treatment options have not been effective. Phase II trials typically comprise up to 100 participants who have already received chemotherapy, surgery, or radiation treatment, but for whom the treatment has not been effective. Participation in Phase II trials is often restricted based on the previous treatment received. Phase III trials usually comprise hundreds to thousands of participants. This large number of participants is necessary in order to determine whether there are true differences between the effectiveness of the compounds according to the present invention and the standard treatment. Phase III may comprise patients ranging from those newly diagnosed with cancer to those with extensive disease in order to cover the disease continuum.

One skilled in the art will appreciate that clinical trials should be designed to be as inclusive as possible without making the study population too diverse to determine whether the treatment might be as effective on a more narrowly defined population. The more diverse the population included in the trial, the more applicable the results could be to the general population, particularly in Phase III trials. Selection of appropriate participants in each phase of clinical trial is considered to be within the ordinary skills of a worker in the art.

B. Assessment of Patients Prior to Treatment

Prior to commencement of the study, several measures known in the art can be used to first classify the patients. Patients can first be assessed, for example, using the Eastern Cooperative Oncology Group (ECOG) Performance Status (PS) scale. ECOG PS is a widely accepted standard for the assessment of the progression of a patient's disease as measured by functional impairment in the patient, with ECOG PS 0 indicating no functional impairment, ECOG PS 1 and 2 indicating that the patients have progressively greater functional impairment but are still ambulatory and ECOG PS 3 and 4 indicating progressive disablement and lack of mobility. Patients' overall quality of life can be assessed, for example, using the McGill Quality of Life Questionnaire (MQOL) (Cohen et al (1995) *Palliative Medicine* 9: 207-219). The MQOL measures physical symptoms; physical, psychological and existential well-being; support; and overall quality of life. To assess symptoms such as nausea, mood, appetite, insomnia, mobility and fatigue the Symptom Distress Scale (SDS) developed by McCorkle and Young ((1978) *Cancer Nursing* 1: 373-378) can be used. Patients can also be classified according to the type and/or stage of their disease and/or by tumour size.

C. Pharmacokinetic Monitoring

To fulfill Phase I criteria, distribution of the compound is monitored, for example, by chemical analysis of samples, such as blood or urine, collected at regular intervals. For example, samples can be taken at regular intervals up until about 72 hours after the start of infusion. In one embodiment, samples are taken at 0, 0.33, 0.67, 1, 1.25, 1.5, 2, 4, 6, 8, 12, 24, 48 and 72 hours after the start of each infusion of compound.

If analysis is not conducted immediately, the samples can be placed on dry ice after collection and subsequently transported to a freezer to be stored at −70° C. until analysis can be conducted. Samples can be prepared for analysis using standard techniques known in the art and the amount of compound present can be determined, for example, by high-performance liquid chromatography (HPLC).

Pharmacokinetic data can be generated and analyzed in collaboration with an expert clinical pharmacologist and used to determine, for example, clearance, half-life and maximum plasma concentration.

D. Monitoring of Patient Outcome

The endpoint of a clinical trial is a measurable outcome that indicates the effectiveness of a compound under evaluation. The endpoint is established prior to the commencement of the trial and will vary depending on the type and phase of the clinical trial. Examples of endpoints include, for example, tumour response rate—the proportion of trial participants whose tumour was reduced in size by a specific amount, usually described as a percentage; disease-free survival—the amount of time a participant survives without cancer occurring or recurring, usually measured in months; overall survival—the amount of time a participant lives, typically measured from the beginning of the clinical trial until the time of death. For advanced and/or metastatic cancers, disease stabilization—the proportion of trial participants whose disease has stabilized, for example, whose tumour(s) has ceased to grow and/or metastasize, can be used as an endpoint. Other endpoints include toxicity and quality of life.

Tumour response rate is a typical endpoint in Phase II trials. However, even if a treatment reduces the size of a participant's tumour and lengthens the period of disease-free survival, it may not lengthen overall survival. In such a case, side effects and failure to extend overall survival might outweigh the benefit of longer disease-free survival. Alternatively, the participant's improved quality of life during the tumour-free interval might outweigh other factors. Thus, because tumour response rates are often temporary and may not translate into long-term survival benefits for the participant, response rate is a reasonable measure of a treatment's effectiveness in a Phase II trial, whereas participant survival and quality of life are typically used as endpoints in a Phase III trial.

VIII. Kits

The present invention additionally provides for therapeutic kits containing one or more compounds of the present invention. In one embodiment, the therapeutic kits are for use in the treatment of cancer. The contents of the kit can be lyophilized and the kit can additionally contain a suitable solvent for reconstitution of the lyophilized components. Individual components of the kit would be packaged in separate containers and, associated with such containers, can be a notice in the form prescribed by a governmental agency regulating the manufacture, use or sale of pharmaceuticals or biological products, which notice reflects approval by the agency of manufacture, for use or sale for human or animal administration.

When the components of the kit are provided in one or more liquid solutions, the liquid solution can be an aqueous solution, for example a sterile aqueous solution. For in vivo use, the compounds may be formulated into a pharmaceutically acceptable syringeable composition. In this case the container means may itself be an inhalant, syringe, pipette, eye dropper, or other such like apparatus, from which the formulation may be applied to an infected area of the subject, such as the lungs, injected into an subject, or even applied to and mixed with the other components of the kit.

Pharmaceutical kits or packs comprising one or more compound of the present invention in combination with one or more standard chemotherapeutic for combination therapy applications are also contemplated by the present invention.

The invention will now be described with reference to specific examples. It will be understood that the following examples are intended to describe embodiments of the invention and are not intended to limit the invention in any way.

EXAMPLES

Example 1

Preparation of Compounds

Some exemplary isolation and purification as well as synthetic methods useful for preparing the present compounds or the intermediates thereof are described below.

Exemplary compounds of formula (I) have been prepared according to Scheme (I) shown below:

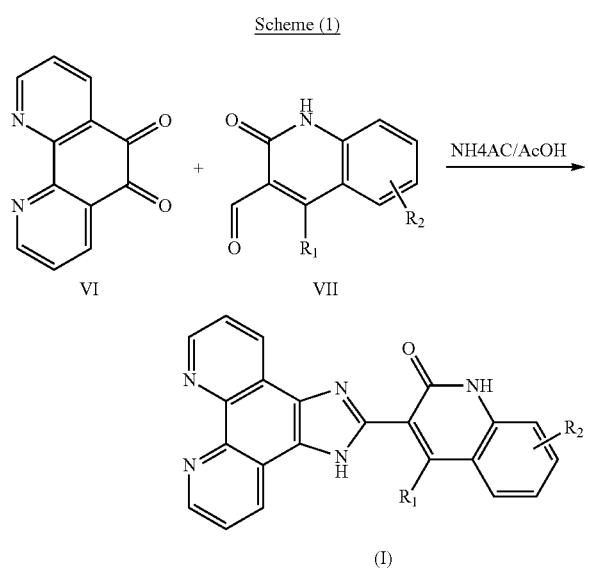

In a typical procedure 1 mmol (1quiv) of 1,10-phenanthroline-5,6-dione was refluxed with equimolar quantity of the corresponding aldehyde and ammonium acetate 10.5 mmol (10.5 equiv.) in glacial acetic acid. The reaction process was monitored by TLC, until complete consumption of the regent was achieved. After completion of the reaction, the reaction was cooled to room temperature and diluted with chilled water at 10 to 15c. The reaction mixture was basified with ammonium hydroxide to pH 7 to 7.5 below 20° C. The separated precipitate was filtered, washed with water and then chilled ethanol, and dried to give desire product.

Aldehydes of formula (VII) were prepared according to the following Scheme 2:

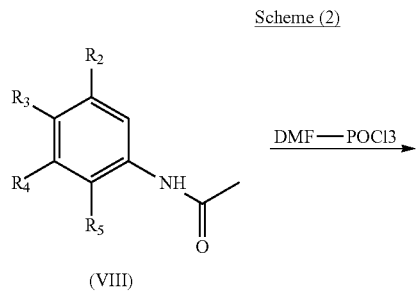

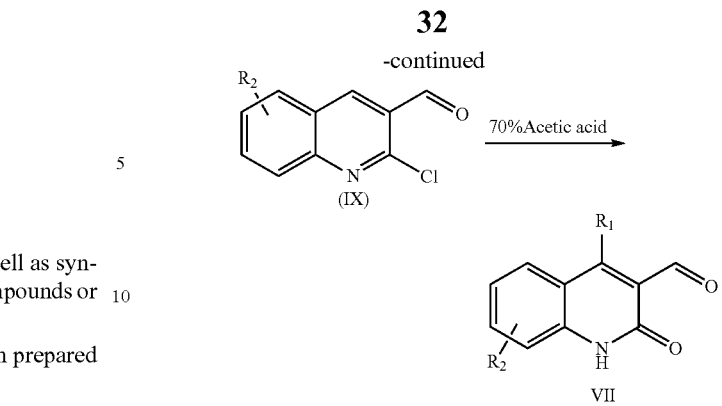

In a typical experimental procedure (*Indian Journal of chemistry Vol,* 44 B pp. 1868-1875) 60 mmoles of POCl$_3$ was added drop wise to the stirred solution of the appropriate phenyl acetamide VIII (which is prepared reacting acetic anhydride with corresponding aniline) in dry dimethyl formamide (DMF) at 0-5° C. The mixture was stirred at room temperature for 0.5 h and at 80-90° C. for 8-10 h then cooled to room temperature, poured into crushed ice and stirred for 0.5 h. The resulting solid was filtered, washed well with water and dried, recrystallized from suitable solvent to give compound IX.

A suspension of Compound IX in 70% acetic acid was heated under reflux for 8 h. The reaction process was monitored by TLC, until complete consumption of the regent was achieved. After completion of the reaction, the reaction was cooled to room temperature and the precipitation was filtered, dried and recrystallized using DMF furnished compound (V)

Exemplary compounds of formula (I) have also been prepared according to Scheme (3) shown below:

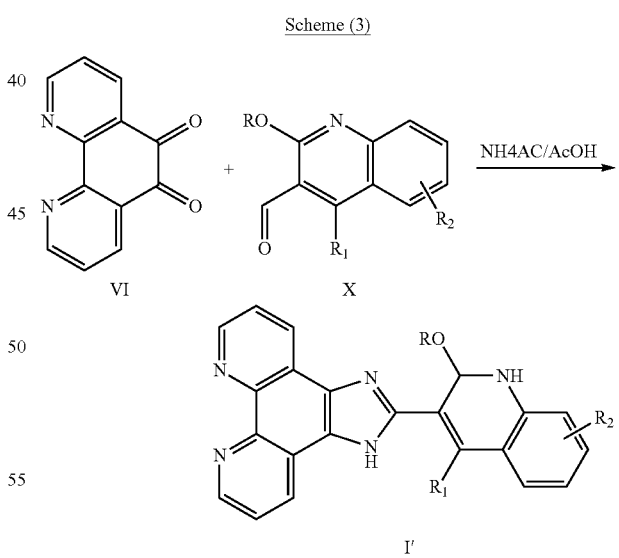

In a typical procedure 1 mmol (1quiv) of 1,10-phenanthroline-5,6-dione was refluxed with equimolar quantity of the corresponding aldehyde and ammonium acetate 10.5 mmol (10.5 equiv.) in glacial acetic acid. The reaction process was monitored by TLC, until complete consumption of the regent was achieved. After completion of the reaction, the reaction was cooled to room temperature and diluted with chilled water at 10 to 15c. The reaction mixture was basified with ammonium hydroxide to pH 7 to 7.5 below 20° C. The separated precipitate was filtered, washed with water and then chilled ethanol, and dried to give desired product.

Aldehydes of formula (X) were prepared according to the following Scheme (4)

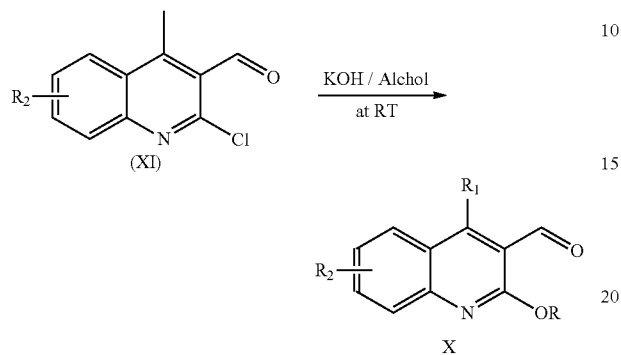

A solution of compound XI (0.1 g), in KOH (1 g) in appropriate anhydrous alcohol (20 times) was stirred for 24 h at room temperature until the starting material was disappeared. The mixture was then poured into crushed ice and neutralized with 2 N HCl. the precipitate was filtered off, dried and purified by flash column chromatography using 5-10% ethyl acetate in hexane. Evaporation of solvent gave the desired aldehyde.

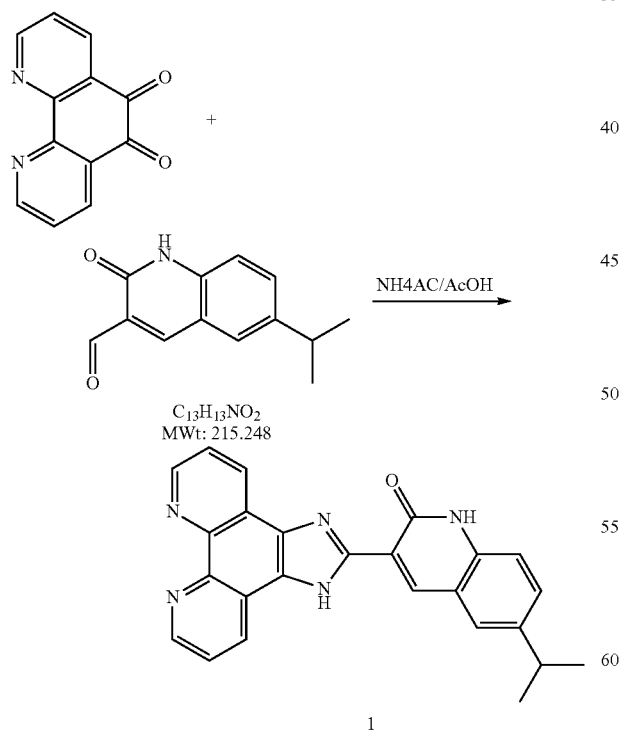

The suspension of 1,10-phenanthroline-5,6-dione (compound V) (0.1 g) and 2-oxo-6(propan-2yl)-1,2-dihydroquinoline-3-carbaldehyde (0.102 g) was refluxed for 2-3 h in acetic acid (15 ml in the presences of ammonium acetate (0.384 g). The reaction was cooled to room temperature and diluted with water (50 ml) at 10-15c. the reaction mixture was basified with ammonium hydroxide to pH 7-7.5 below 20° C. The separated precipitate was filtered and wash with water, chilled ethanol and such dried to get the desired product (1.1 g yield 57%) as light yellow solid LCMS M/z 406 M+H The structures of additional exemplary compounds are listed below as specific embodiments of Formula (I) and Formula (IV).

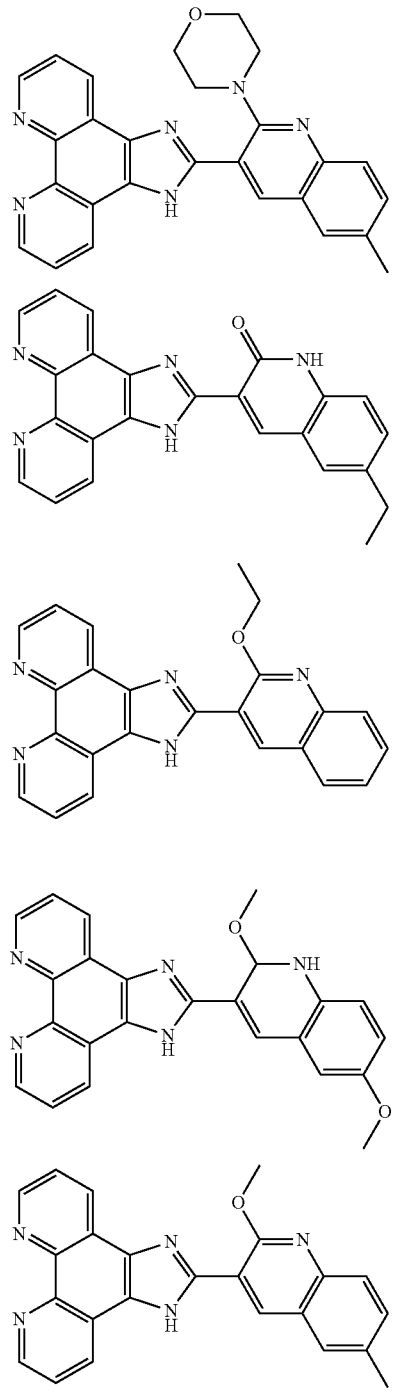

-continued

TABLE 3

Antiproliferative activity of exemplary compounds of formulae (I) to (IV)

| Compound | Kidney ACHN | Kidney CAKI-1 | Pancreas BXPC3 | Pancreas SU-86-86 | Pros. DU14 | Colon KM12 | Colon HT-29 | Leuk. HL60 | Brain SK-N-AS | Brain U87-MG | NSCLC H226 | NSCLC HOP-92 | NSCLC HOP-62 | NSCLC H460 | NSCLC EKVX |
|---|---|---|---|---|---|---|---|---|---|---|---|---|---|---|---|
| 1 | 0.17 | 0.156 | 0.18 | 0.18 | 0.17 | 0.33 | 0.35 | 0.03 | 0.21 | 0.19 | 0.41 | 0.16 | 0.21 | 0.16 | 0.22 |
| 2 | 0.17 | ND | 0.18 | ND | 0.22 | 0.22 | 0.3 | 0.38 | ND | 0.18 | 0.43 | 0.17 | ND | ND | ND |
| 3 | 0.17 | ND | 0.18 | ND | 0.17 | 0.23 | 0.22 | 0.15 | ND | 0.154 | 0.39 | 0.17 | ND | ND | ND |
| 4 | 0.127 | 0.17 | 0.17 | 0.026 | 0.15 | 0.18 | 0.3 | 0.17 | 0.19 | 0.18 | 0.39 | 0.17 | 0.17 | 0.16 | 0.16 |
| 5 | 0.13 | ND | 0.2 | 0.028 | 0.18 | 0.28 | 0.17 | 0.11 | 0.09 | 0.18 | 0.19 | 0.17 | 0.21 | 0.14 | 0.15 |
| 6 | 0.038 | 0.03 | 0.2 | 0.026 | 0.13 | 0.18 | 0.17 | 0.05 | 0.036 | 0.18 | 0.21 | 0.03 | 0.03 | 0.16 | 0.17 |
| 7 | 0.023 | 0.16 | 0.04 | 0.11 | 0.03 | 0.4 | 0.39 | 0.03 | 0.19 | 0.04 | 0.2 | 0.17 | 0.15 | 0.32 | 0.22 |
| 8 | 0.203 | ND | 0.21 | ND | 0.15 | 0.583 | 0.285 | 0.11 | ND | 0.19 | 0.71 | 0.16 | ND | ND | ND |

-continued

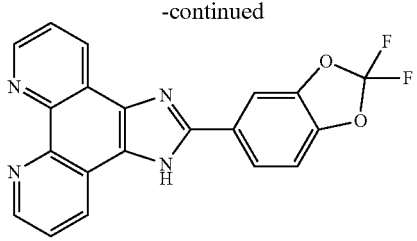

Example 2

In Vitro Inhibition of Proliferation

Cell Proliferation Study on Human Cancer Cells

Exemplary compounds 1-8 were tested for anti-cancer activity in vitro using human renal cancer cells (ACHN and CAK-1), human pancreatic cells (BXPC3 and SU-86-86), human prostate cancer cell (DU14), human colon carcinoma cells (HT-29 and KM-12), leukemia cells (HL60), brain cancer/tumour cells (SK-A-AS, U87-MG), and human non-small cell lung cancer cells (H460). Compounds 1-8 are the specific embodiments of Formula (I) and Formula (IV) as described above in this application.

The cells were maintained as a monolayer in a growth medium; McCoy's 5A modified medium (Sigma, St. Louis, Mo.), supplemented with 2 mM L-glutamine (Gibco, Grand Island, N.Y.), 10% fetal bovine serum (FBS) (Multicell, WISENT Inc. St-Bruno, QC), antibiotic-antimycotic (Multicell), at 37° C. in a 5% $CO_2$-humidified incubator. Cells were transferred onto 150 mm tissue culture plates and grown until sub-confluency (70-80%) prior to their use. The in vitro antiproliferative activity of compounds was evaluated by incubating the cells with varying concentrations of exemplary compounds as shown in Table 1 for 5 days. The efficacy of these compounds in this cell proliferation assay was measured based in the ability of live cells to reduce the tetrazolium salt XTT to orange colored compounds of formazan (XTT cell proliferation kit IT, Roche Applied Science, Montreal, QC). Results of these experiments are shown in Table 3.

Cell Proliferation Study on Human and Mouse Lymphoma Cells

In this study, compounds 1-8 were screened in vitro against a panel of four mouse lymphoma cell lines and two human lymphoma cell line for cell growth inhibition activity. Following treatment, half maximal inhibitory concentrations ($IC_{50}$) were determined with the objective of selecting the most efficacious compounds for evaluation of in vitro absorption, distribution, metabolism, and excretion (ADME) screening.

Cell Lines

Human Burkitt's lymphoma Raji cells (ATCC CCL-86) were grown in suspension in Roswell Park Memorial Institute (RPMI) 1640 medium supplemented with 10% fetal bovine serum (FBS), 10 mM HEPES KOH pH 7.4, and 2 mM sodium pyruvate at 37° C. in an atmosphere of 5% $CO_2$ in air. Logarithmically growing cells were routinely sub-cultured twice weekly. Briefly, cells were collected by centrifugation, resuspended in pre-warmed media, and diluted 1:10 into a 75 cm² flask.

Similarly, human Burkitt's lymphoma Ramos cells (ATCC CRL-1596) were grown in suspension in Roswell Park Memorial Institute (RPMI) 1640 medium supplemented with 10% fetal bovine serum (FBS), 10 mM HEPES KOH pH 7.4, and 2 mM sodium pyruvate. Mouse P388D1 (ATCC CCL-46) and WR19L (ATCC TIB-52) cells were grown in suspension in Dulbecco's Modified Eagle Medium (DMEM) with 10% fetal bovine serum (FBS), 10 mM HEPES, and 2 mM sodium pyruvate. Mouse WEHI231 (ATCC CRL-1702) and EL4 (ATCC TIB-39) cells were grown in suspension in DMEM with 10% fetal bovine serum (FBS), 10 mM HEPES KOH pH 7.4, 2 mM sodium pyruvate, and 0.05 mM β-mercaptoethanol. All cells were maintained at 37° C. in an atmosphere of 5% $CO_2$ in air. Logarithmically growing cells were routinely sub-cultured twice weekly. Briefly, cells were collected by centrifugation, resuspended in pre-warmed media, and diluted 1:10 into a 75 cm² flask.

TABLE 4

Cell lines screened for in vitro potency

| Cell Line | Media | Supplements |
|---|---|---|
| Ramos (Human Burkitt's lymphoma) | RPMI-1640 | 10% FBS, 10 mM HEPES, 2 mM sodium pyruvate |
| P388D1 (mouse, lymphoma) | DMEM | 10% FBS, 10 mM HEPES, 2 mM sodium pyruvate |
| WR19L (mouse, lymphoma) | DMEM | 10% FBS, 10 mM HEPES, 2 mM sodium pyruvate |
| WEHI 231 (mouse, B-cell lymphoma) | DMEM | 10% FBS, 10 mM HEPES, 2 mM sodium pyruvate, 0.05 mM β-mercaptoethanol |
| EL4 (mouse, lymphoma) | DMEM | 10% FBS, 10 mM HEPES, 2 mM sodium pyruvate, 0.05 mM β-mercaptoethanol |

Cell Growth Inhibition Assay

Cells were subcultured and $4 \times 10^3$ cells (in 50 μL) were transferred to each well in a Falcon 96-well tissue culture plate. Exemplary compounds were dissolved in pure dimethyl sulphoxide (DMSO) at a concentration of 10 mM. From this 10 mM stock solution, 12 successive serial dilutions were made in DMSO (2.5 fold dilutions), ranging from 0.52 μM to 10 mM. Using these stock dilutions, 5 μL of each were added to 500 μL of media, and 50 μL of this was added to the cells. The final concentrations being tested ranged from 0.0026 μM to 50 μM. Each concentration was tested in triplicate, and DMSO and untreated cells were also included as controls. After five days of incubation with the compounds, cell viability was determined using the XTT cell proliferation kit (Roche, Cat. No. 11 465 015 001). Following the XTT protocol, 4.5-24 hours after addition of the reagent, the plates were read in a μQuant 96-well plate spectrophotometer (Biotek Instruments Inc.) and the results analyzed to determine the $IC_{50}$.

Results

In vitro potency was assessed using eight exemplary compounds against a panel of human and mouse lymphoma cell lines (Table 4). All of the compounds effectively inhibited the growth of model cells lines with $IC_{50}$ values in the sub-micromolar range (Ramos $IC_{50}$ from 0.018 to 0.163 μM; EL4 $IC_{50}$ from 0.057 to 0.518 μM; P388D1 $IC_{50}$ from 0.052 to 0.414 μM; WEHI231 $IC_{50}$ from 0.0030 to 0.0126 μM; WR19L $IC_{50}$ from <0.0026 to 0.082 μM; from Table 5). To compare the efficacy of the compounds in cell growth inhibition across the entire panel of cell lines screened, the eight compounds were ranked according to efficacy against each cell line with a numerical value of one indicating most efficacious (lowest $IC_{50}$ value) and eight being the least efficacious (highest $IC_{50}$ value). A compound that is consistently the most active in inhibiting cell growth would be expected to have a mean rank of nearly one with a low standard deviation indicating low variation from its top ranked position. Of the compounds tested, the most potent candidates were Compounds 6, 8, 4 and 7, which had mean rankings of 1.3, 1.7, 4.2, and 4.8, respectively (see Table 6). Compounds 6 and 8 were consistently the most effective compounds as the standard deviations of their mean rankings were low (0.5) indicating invariance from their top rankings. The least potent of the panel of compounds was Compound 1 (mean rank of 6.2).

TABLE 5

In vitro screening of eight compounds

| | Compound | | | | | | | |
|---|---|---|---|---|---|---|---|---|
| | 1 | 2 | 3 | 4 | 5 | 6 | 7 | 8 |
| Raji (hs) | 0.153 μM | 0.166 μM | 0.197 μM | 0.054 μM | 0.109 μM | 0.032 μM | 0.112 μM | 0.025 μM |
| Ramos (hs) | 0.163 μM | 0.150 μM | 0.139 μM | 0.058 μM | 0.075 μM | 0.018 μM | 0.083 μM | 0.034 μM |
| EL4 (ms) | 0.483 μM | 0.384 μM | 0.451 μM | 0.486 μM | 0.518 μM | 0.057 μM | 0.470 μM | 0.199 μM |
| P388D1 (ms) | 0.370 μM | 0.400 μM | 0.377 μM | 0.243 μM | 0.414 μM | 0.052 μM | 0.209 μM | 0.146 μM |
| WEHI231 (ms) | 0.0052 μM | 0.0051 μM | 0.0042 μM | 0.0064 μM | 0.0126 μM | 0.0042 μM | 0.0076 μM | 0.0030 μM |
| WR19L (ms) | 0.082 μM | 0.031 μM | 0.059 μM | 0.0058 μM | 0.0093 μM | <0.0026 μM | 0.012 μM | 0.0051 μM |
| Mean $IC_{50}$ | 0.209 μM | 0.189 μM | 0.205 μM | 0.142 μM | 0.190 μM | 0.028 μM | 0.149 μM | 0.069 μM |

TABLE 6

Ranking of efficacy of eight compounds

| | Compound | | | | | | | |
|---|---|---|---|---|---|---|---|---|
| | 1 | 2 | 3 | 4 | 5 | 6 | 7 | 8 |
| Raji (hs) | 6 | 7 | 8 | 3 | 4 | 2 | 5 | 1 |
| Ramos (hs) | 8 | 7 | 6 | 3 | 4 | 1 | 5 | 2 |
| EL4 (ms) | 6 | 3 | 4 | 7 | 8 | 1 | 5 | 2 |
| P388D1 (ms) | 5 | 7 | 6 | 4 | 8 | 1 | 3 | 2 |
| WEHI231 (ms) | 4 | 3 | 2 | 5 | 7 | 2 | 6 | 1 |
| WR19L (ms) | 8 | 6 | 7 | 3 | 4 | 1 | 5 | 2 |
| Mean Rank | 6.2 ± 1.6 | 5.5 ± 2.0 | 5.5 ± 2.2 | 4.2 ± 1.6 | 5.8 ± 2.0 | 1.3 ± 0.5 | 4.8 ± 1.0 | 1.7 ± 0.5 |

Example 3

In Vivo Efficacy of Compound 1 in a Colon Carcinoma Xenograft Model

The ability of compound 1 to inhibit colon tumour growth in vivo was tested as follows. CD-1 female nude mice (7 mice per treatment group, 6-7 weeks) were injected intraperitoneally with human colon adenocarcinoma cells HT-29 cells ($3 \times 10^6$ cells in 0.1 ml PBS). Treatment of the mice with vehicle or 50 mg/kg/d of compound 3 was initiated 5 days post-inoculation (size of tumours=20-40 mm³) for 7-day cycles of five days followed by a 2 day break for 5 weeks. The size of the tumours was measured over the course of the experiment using calipers, and the weight of the tumours was measured after the animals were sacrificed. Compound 1 was able to inhibit tumour growth, as measured by tumour size, compared to vehicle-treated control animals (See FIG. 1).

Figure 2:
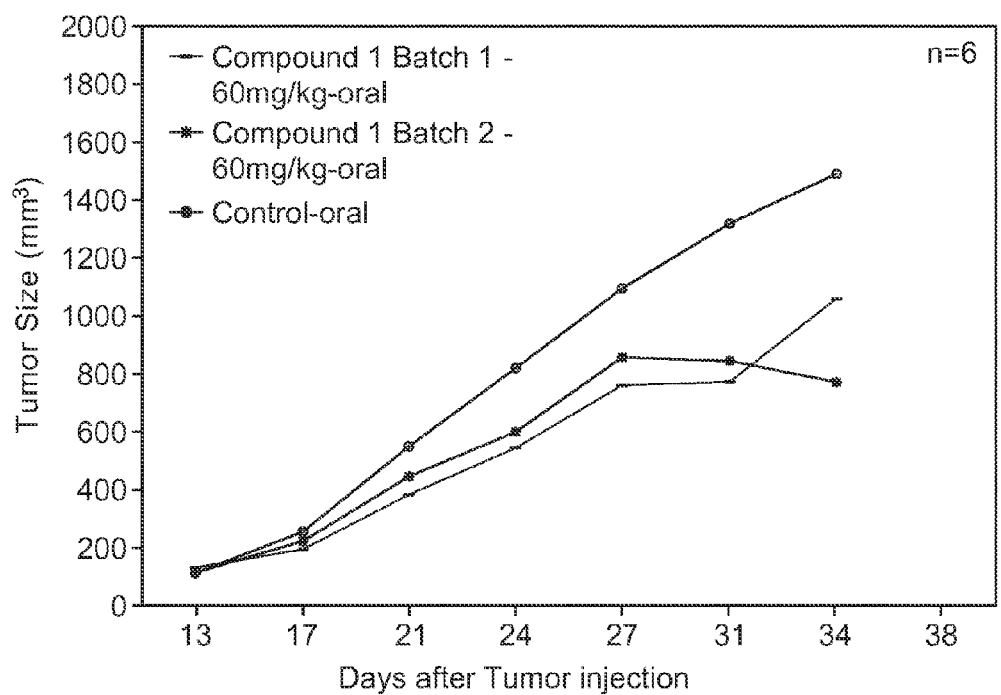
FIG. 2 depicts in vivo efficacy of compound 1 in a colon carcinoma (KM-12) xenograft model.
Figure 3:
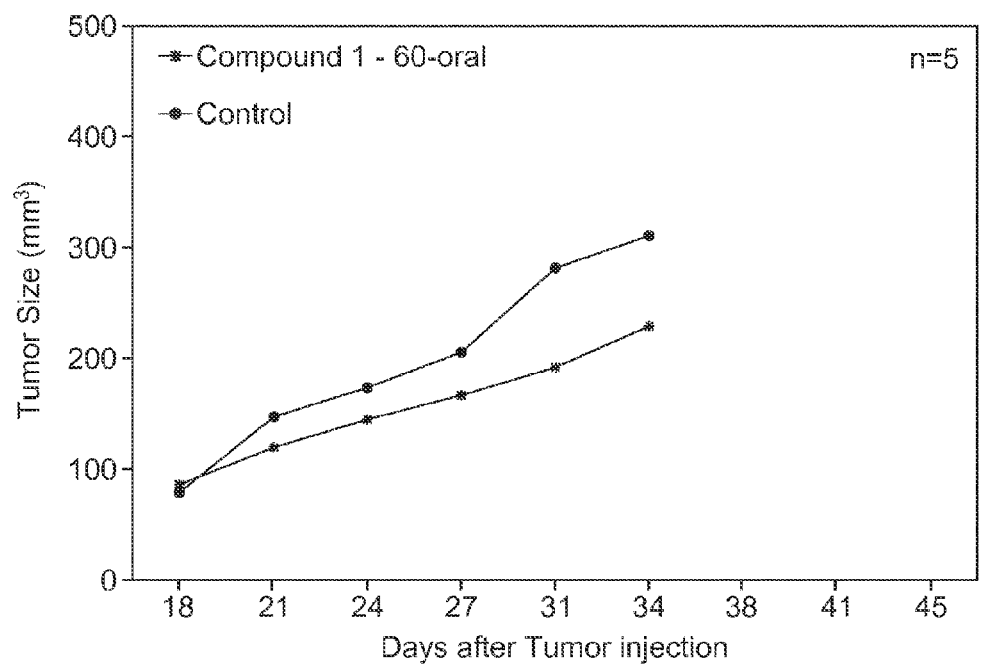
FIG. 3 depicts in vivo efficacy of compound 1 in a colon carcinoma (SW-620) xenograft model.

Similar tests were conducted with colon carcinoma KM-12 cells and colon carcinoma SW-620 cells. The results of these tests are shown in FIGS. 2 and 3, which indicate that Compound 1 was able to inhibit tumour growth, as measured by tumour size, compared to vehicle-treated control animals.

Figure 4:
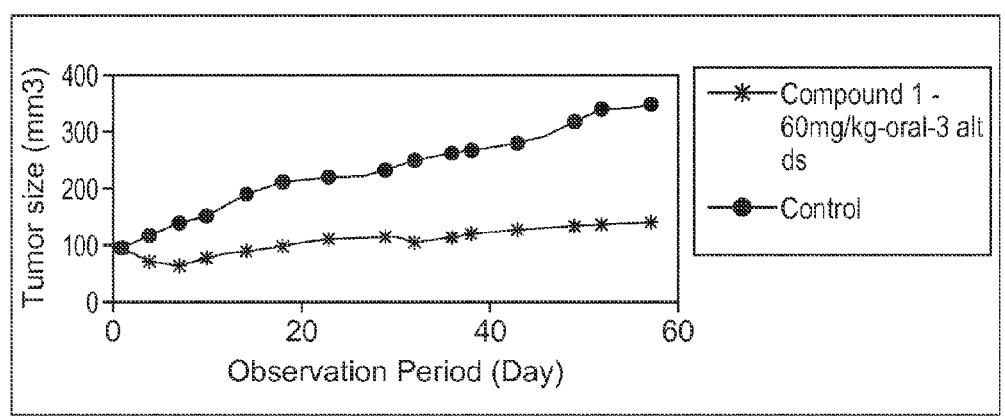
FIG. 4 depicts in vivo efficacy of compound 1 in a renal cell carcinoma (ACHN) xenograft model.
Figure 5:
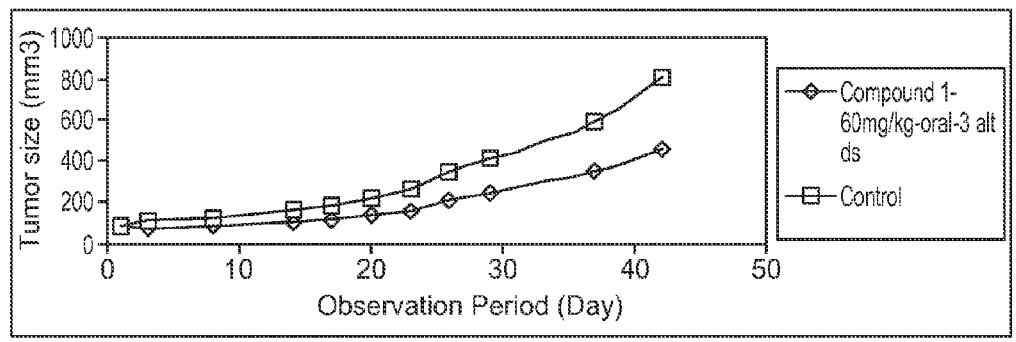
FIG. 5 depicts in vivo efficacy of compound 1 in a pancreatic cancer (BxPC-3) xenograft model.
Figure 6:
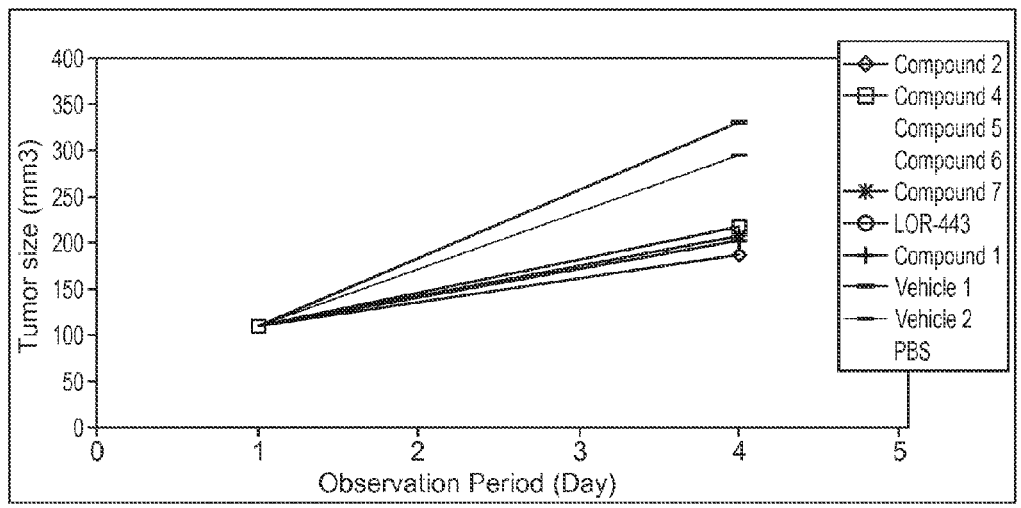
FIG. 6 depicts in vivo efficacy of certain compounds of formula (I) in a non small cell lung cancer (H460) xenograft model.
Figure 7:
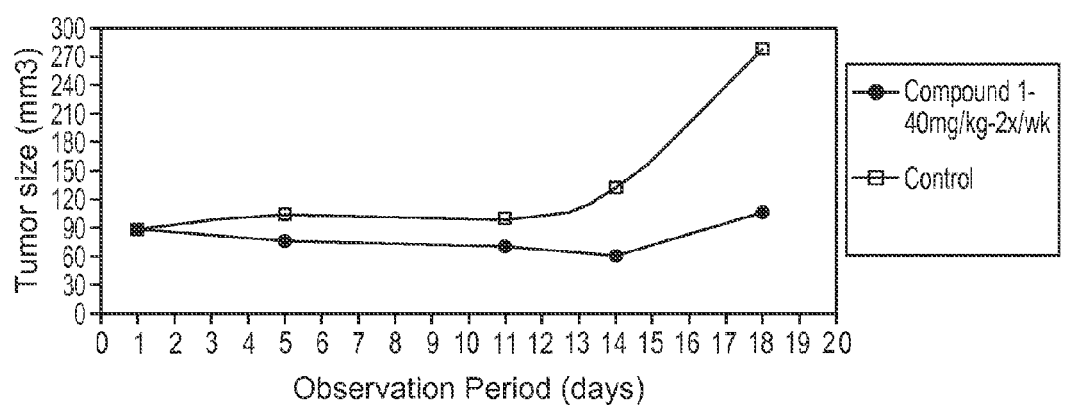
FIG. 7 depicts in vivo efficacy of compound 1 in a Glioplastoma (U87-MG) xenograft model.

The ability of compound 1 to inhibit renal cell carcinoma growth (see FIG. 4), to inhibit pancreatic carcinoma growth (FIG. 5), to inhibit large-cell lung carcinoma cell growth (FIG. 6), and to inhibit Glioblastoma cell growth (FIG. 7) was also tested following the general procedure as discussed above. The results from these tests indicate that Compound 1 was able to inhibit tumour growth, as measured by tumour size, compared to vehicle-treated control animals.

The disclosure of all patents, publications, including published patent applications, and database entries referenced in this specification are specifically incorporated by reference in their entirety to the same extent as if each such individual patent, publication, and database entry were specifically and individually indicated to be incorporated by reference.

Although the invention has been described with reference to certain specific embodiments, various modifications thereof will be apparent to those skilled in the art without departing from the spirit and scope of the invention as outlined in the claims appended hereto.

We claim:
1. A compound of formula (I):

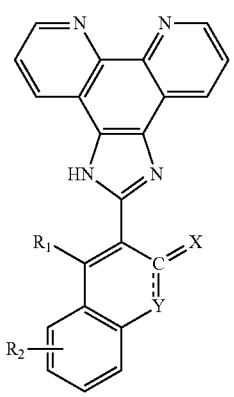

(I)

or a salt or solvate thereof, wherein:
- --- between C and X, and between C and Y designates a single or a double bond, and at least one of --- is a single bond;
- X is optionally substituted alkoxy or $NR_3R_4$ when --- between C and X is single bond, or
- X is O when --- between C and X is a double bond;
- Y is N when --- between C and Y is a double bond, or Y is NH, when --- between C and Y is a single bond;
- $R_1$ and $R_2$ are independently H, optionally substituted alkyl, or optionally substituted alkoxy, and
- $R_3$ and $R_4$ are taken together to form a 5 or 6 membered optionally substituted heterocycle, having at least one heteroatom that is N or O; and
- provided that when X is O and --- between C and X is a double bond; then $R_1$ and $R_2$ both are not H.

2. The compound of claim 1, wherein $R_1$ and $R_2$ are independently H, C1-C6 alkyl, or —O—C1-C6 alkyl.

3. The compound of claim 1, wherein $R_1$ is H and $R_2$ is C1-C6 alkyl, or —O—C1-C6 alkyl.

4. The compound of claim 1, wherein $R_1$ and $R_2$ are H.

5. The compound of claim 1, wherein X is —O—C1-C6 alkyl or $NR_3R_4$ and --- between C and X is single bond.

6. The compound of claim 1, wherein the compound has the structural formula:

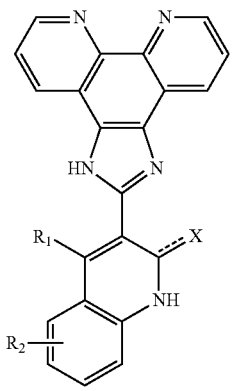

(II)

or a salt or solvate thereof, wherein:
- --- designates a single or a double bond;
- X is optionally substituted alkoxy or $NR_3R_4$ when --- is single bond, or
- X is O when --- is a double bond;
- $R_1$ and $R_2$ are independently H, optionally substituted alkyl, or optionally substituted alkoxy; and
- $R_3$ and $R_4$ are taken together to form a 5 or 6 membered optionally substituted heterocycle, having at least one heteroatom that is N or O; and
- provided that when X is O and --- between C and X is a double bond; then $R_1$ and $R_2$ both are not H.

7. The compound of claim 6, wherein X is —O—C1-C6 alkyl or $NR_3R_4$, when --- is single bond; or X is O when --- is double bond.

8. The compound of claim 6, wherein $R_1$ and $R_2$ are independently H, C1-C6 alkyl, or —O—C1-C6 alkyl.

9. The compound of claim 6, wherein $R_1$ is H; and $R_2$ is H, optionally substituted alkyl, or optionally substituted alkoxy.

10. The compound of claim 9, wherein $R_1$ is H; and $R_2$ is H, C1-C6 alkyl, or —O—C1-C6 alkyl.

11. The compound of claim 6, wherein is selected from the group consisting of:

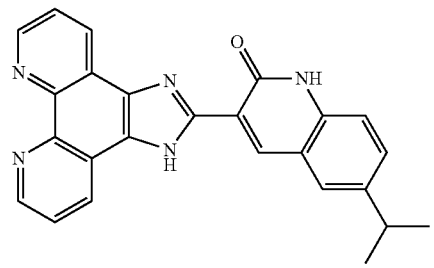

-continued

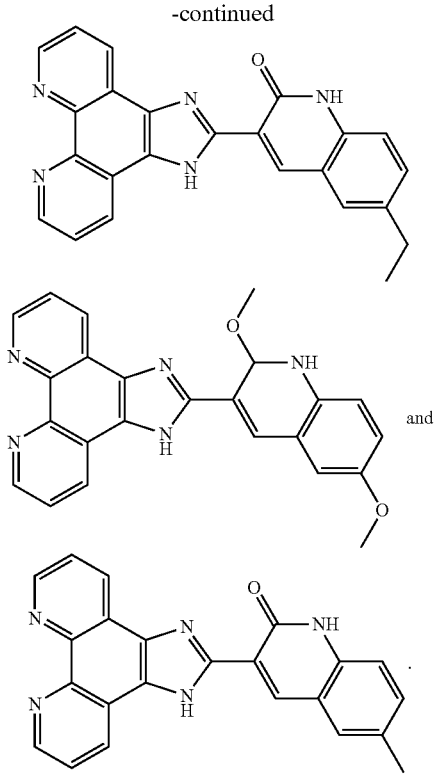

12. The compound of claim 1, wherein the compound has the structural formula:

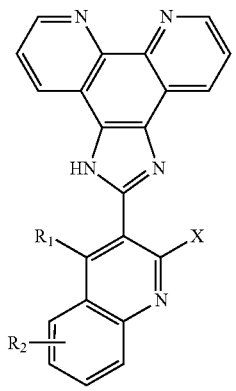

(III)

or a salt or solvate thereof, wherein:
  X is optionally substituted alkoxy or $NR_3R_4$;
  $R_1$ and $R_2$ are independently H, optionally substituted alkyl, or optionally substituted alkoxy; and
  $R_3$ and $R_4$ are taken together to form a 5 or 6 membered optionally substituted heterocycle, having at least one heteroatom that is N or O.

13. The compound of claim 12, wherein $R_1$ and $R_2$ are independently H, C1-C6 alkyl, or —O—C1-C6 alkyl.

14. The compound of claim 13, wherein $R_1$ is H; and $R_2$ is H, C1-C6 alkyl, or —O—C1-C6 alkyl.

15. The compound of claim 12, wherein X is —O—C1-C6 alkyl.

16. The compound of claim 12, wherein X is $NR_3R_4$; and $R_3$ and $R_4$ are taken together to form a 5 or 6 membered heterocycle, having at least one heteroatom that is N or O.

17. The compound of claim 12, wherein is selected from the group consisting of

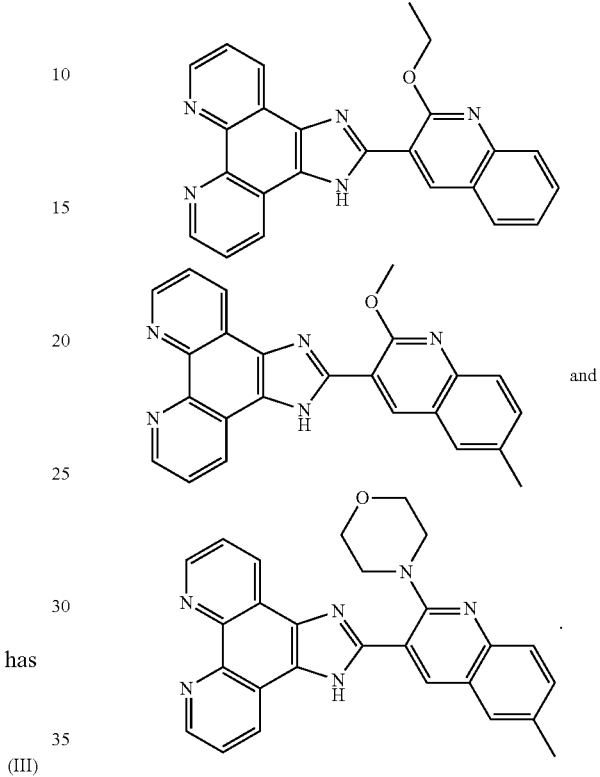

18. A pharmaceutical composition comprising a compound according to claim 1, or a salt or solvate thereof, and a pharmaceutically acceptable carrier.

19. A pharmaceutical composition comprising a compound selected from the compounds of claim 11 or a salt or solvate thereof, and a pharmaceutically acceptable carrier.

20. A method of inhibiting the proliferation of cancer cells in a subject in need thereof, comprising treating the cancer cells with a compound according to claim 1.

21. The method of claim 20, wherein the cancer cells are in vitro.

22. A method of treating cancer in a mammal, comprising administering to said mammal an effective amount of a compound according to claim 1.

23. The method of claim 20, wherein the cancer is renal cancer, pancreatic cancer, prostate cancer, colon cancer, leukemia, lymphoma, brain cancer/tumour or non-small cell lung cancer.

24. The method of claim 20, wherein the cancer is lymphoma.

25. A pharmaceutical composition comprising a compound selected from the compounds of claim 17 or a salt or solvate thereof, and a pharmaceutically acceptable carrier.

26. The method of claim 22, wherein the cancer is renal cancer, pancreatic cancer, prostate cancer, colon cancer, leukemia, lymphoma, brain cancer/tumour or non-small cell lung cancer.

27. The method of claim 26, wherein the cancer is lymphoma.

* * * * *